(12) United States Patent
Green

(10) Patent No.: US 6,221,007 B1
(45) Date of Patent: Apr. 24, 2001

(54) SYSTEM AND METHOD FOR ENDOSCOPIC IMAGING AND ENDOSURGERY

(76) Inventor: Philip S. Green, 820 Miranda Green, Palo Alto, CA (US) 94306-3716

(*) Notice: Subject to any disclaimer, the term of this patent is extended or adjusted under 35 U.S.C. 154(b) by 0 days.

(21) Appl. No.: 09/241,321

(22) Filed: Feb. 1, 1999

Related U.S. Application Data

(63) Continuation-in-part of application No. 08/841,167, filed on Apr. 29, 1997, now Pat. No. 5,928,137.
(60) Provisional application No. 60/021,559, filed on Jul. 11, 1996, and provisional application No. 60/016,830, filed on May 3, 1996.

(51) Int. Cl.[7] ...................................................... A61B 1/04
(52) U.S. Cl. ........................ 600/160; 600/104; 600/106
(58) Field of Search .................................. 600/101, 102, 600/104, 106, 109, 112, 160, 114; 348/65, 71, 74, 75

(56) References Cited

U.S. PATENT DOCUMENTS

| | | |
|---|---|---|
| D. 358,471 | 5/1995 | Cope et al. . |
| 3,945,371 | 3/1976 | Adelman . |
| 4,300,564 | 11/1981 | Furihata . |
| 4,471,766 | 9/1984 | Terayama . |
| 4,538,594 | 9/1985 | Boebel et al. . |
| 4,604,992 | 8/1986 | Sato . |
| 4,653,476 * | 3/1987 | Bonnet ................................ 600/106 |
| 4,742,819 | 5/1988 | George . |
| 4,756,309 | 7/1988 | Sachse et al. . |
| 4,759,348 | 7/1988 | Cawood . |
| 4,879,992 | 11/1989 | Nishigaki et al. . |
| 5,020,514 * | 6/1991 | Heckele ................................ 600/107 |
| 5,089,000 | 2/1992 | Agee et al. . |
| 5,178,536 | 1/1993 | Werly et al. . |
| 5,222,477 | 6/1993 | Lia . |
| 5,373,317 | 12/1994 | Salvati et al. . |

(List continued on next page.)

FOREIGN PATENT DOCUMENTS

| | | |
|---|---|---|
| 4102437 | 4/1992 | (JP) . |
| 9315648 | 8/1993 | (WO) . |

OTHER PUBLICATIONS

Endo View brochure, by Urohealth Co., undated.

Endoscopic Surgery, by R.A. White & S.R. Klein, pp. 42–43, Mosby Year Book, 1991.

Operative Laparoscopic System, by Circon–ACMI Product Literature, 1994.

Adolescent Bronchoscope, Karl Storz Product Literature, Jan. 1990.

*Primary Examiner*—John P. Leubecker

(57) ABSTRACT

An endoscopic surgical system for use in endoscopic surgery including an endosurgical instrument having an elongated shaft and an end-effector operably mounted to a distal end of the shaft. A video endoscope device includes an elongated telescope portion containing a distal viewing face, and a coupling device couples the instrument to the endoscope device. This coupling substantially maintains the relative position of the elongated shaft adjacent the telescope portion such that the endoscope viewing face is rearward of the distal end effector to view the distal end-effector from a position along the shaft. A handle portion is provided operably coupled to the coupling device in a manner enabling the distal end-effector and the viewing face to be manually positioned as a single unit during endoscopic surgery. The handle portion is further configured to manually operate the end-effector. A video display device is operably coupled to the coupling device at a viewing angle and location therealong wherein an image of the end-effector displayed on the display device appears to be a substantially direct view of the end-effector that is positioned in-line with the insertion shaft.

46 Claims, 21 Drawing Sheets

U.S. PATENT DOCUMENTS

| | | |
|---|---|---|
| 5,631,973 | 5/1997 | Green . |
| 5,647,838 | 7/1997 | Bloomer . |
| 5,667,472 | 9/1997 | Finn et al. . |
| 5,667,473 | 9/1997 | Finn et al. . |
| 5,667,478 | 9/1997 | McFarlin et al. . |
| 5,725,478 * | 3/1998 | Saad ................... 600/109 |
| 5,785,644 * | 7/1998 | Grabover et al. ............ 600/131 |
| 5,879,289 * | 3/1999 | Yarush et al. ............... 600/109 |
| 5,891,013 * | 4/1999 | Thompson .................. 600/114 |

* cited by examiner

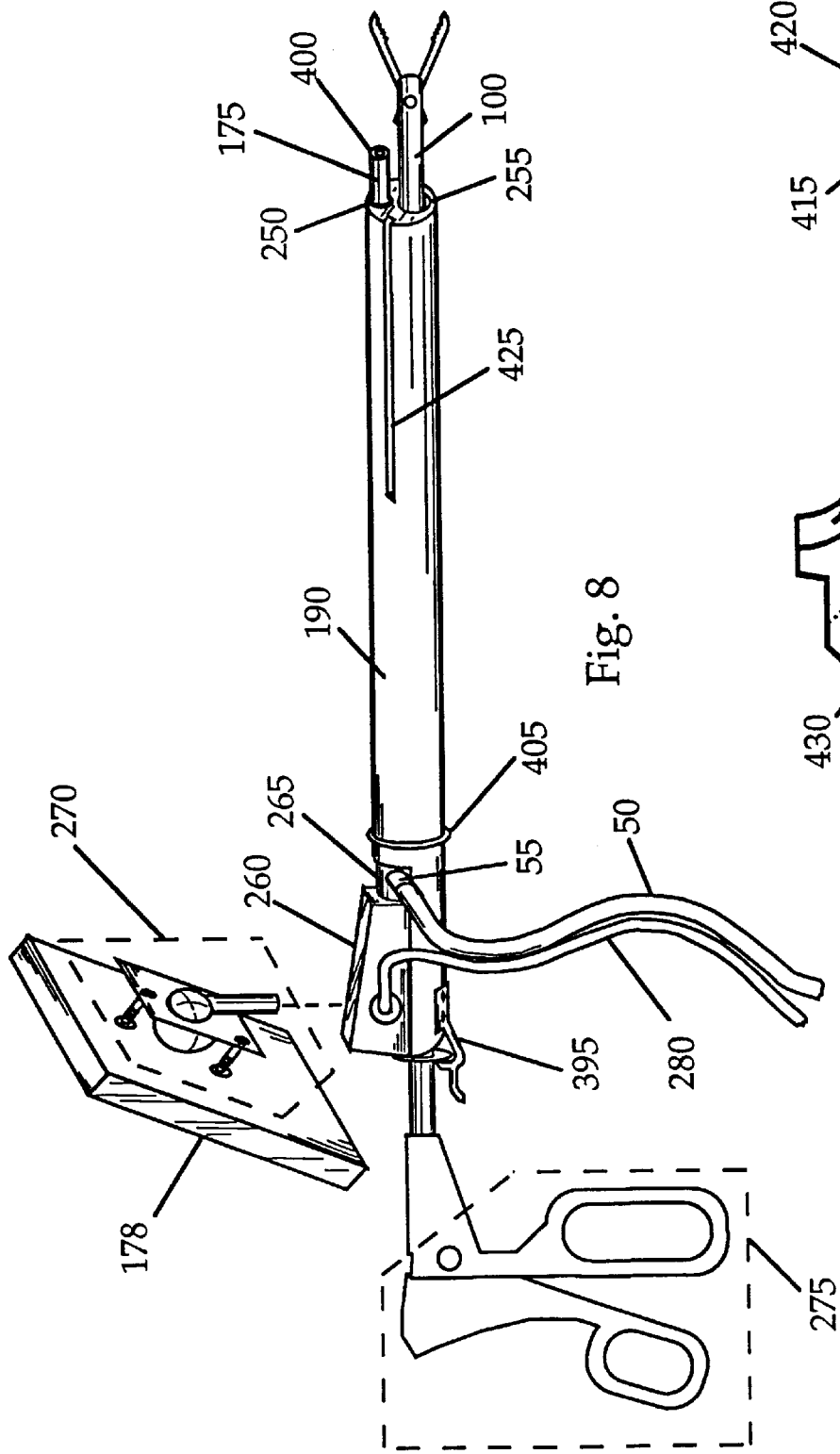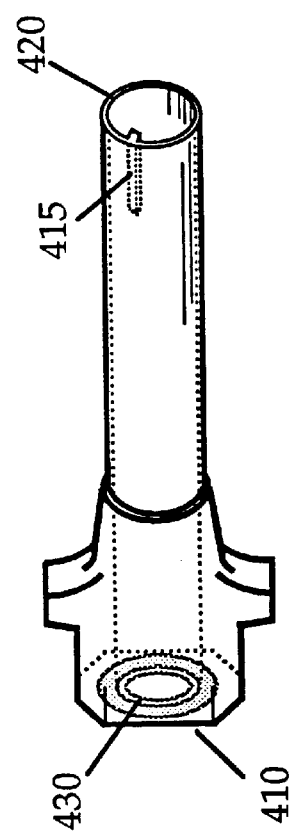

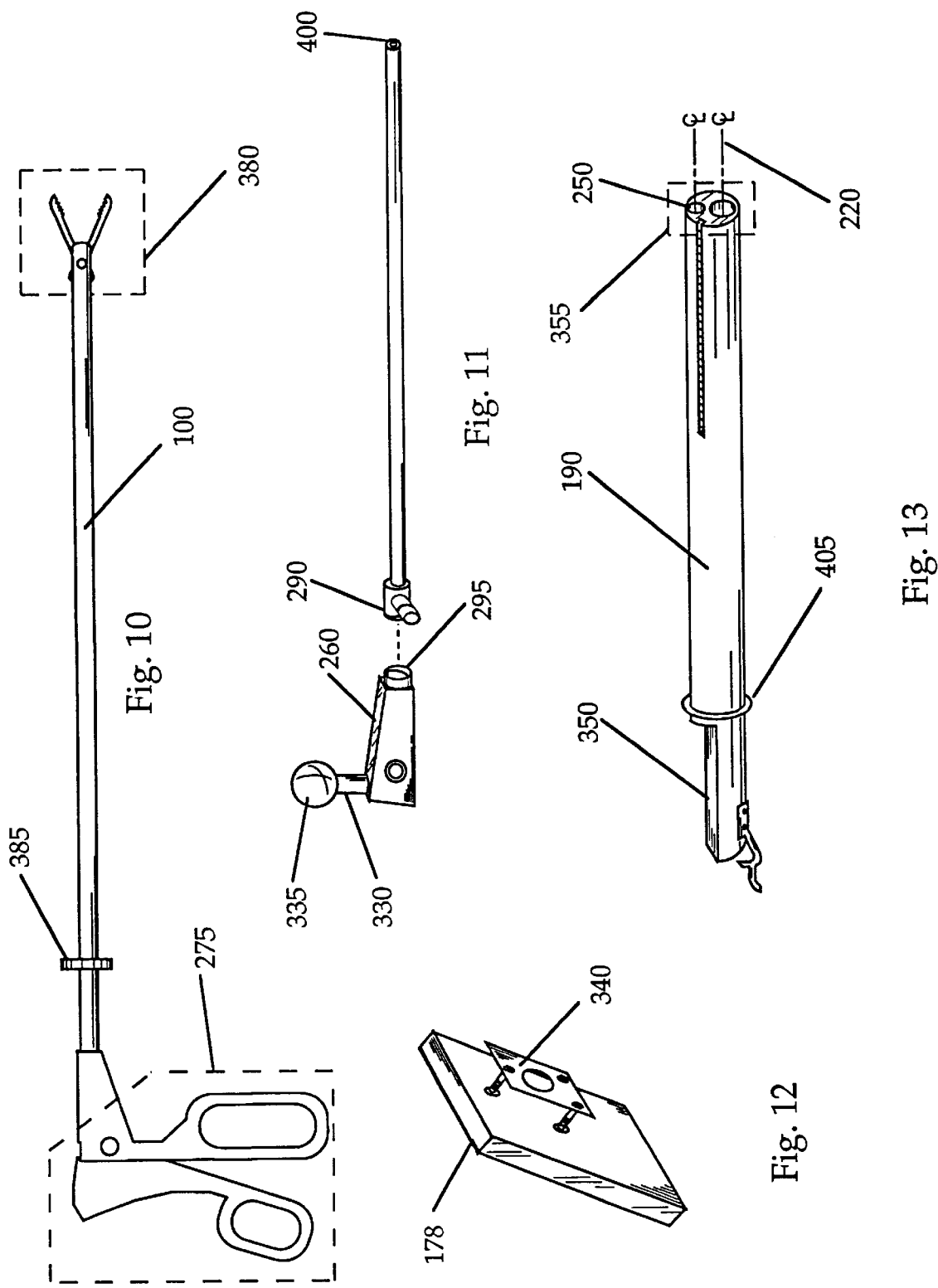

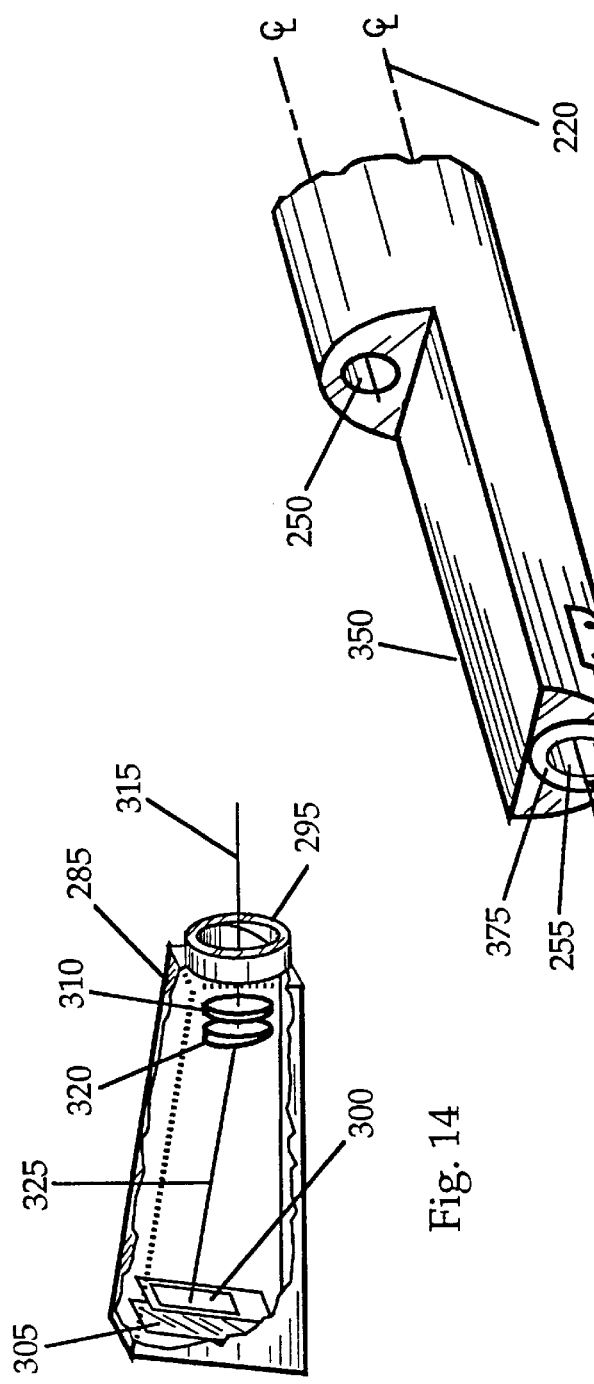
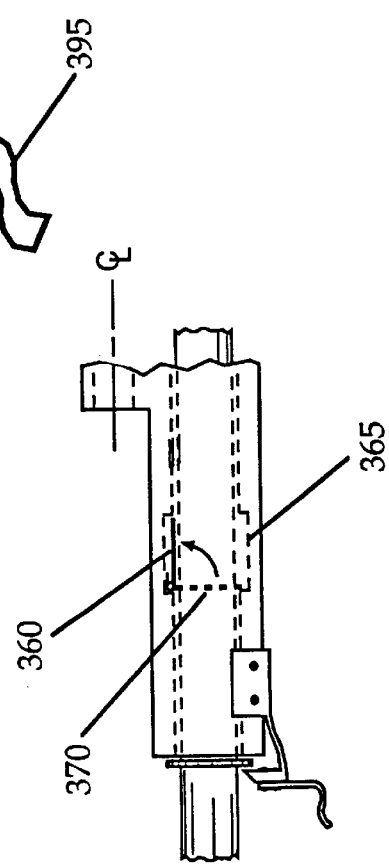
Fig. 14
Fig. 15
Fig. 16

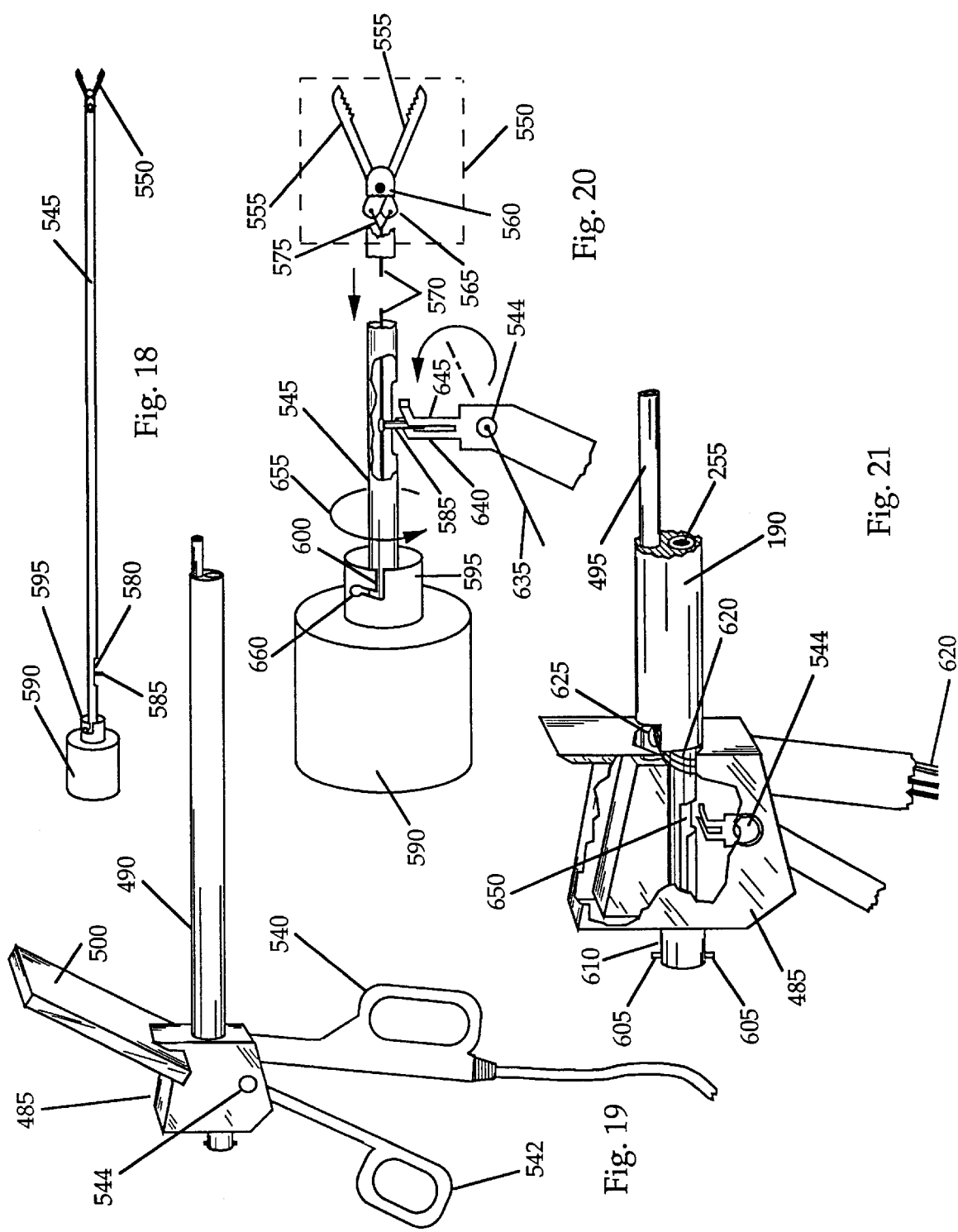

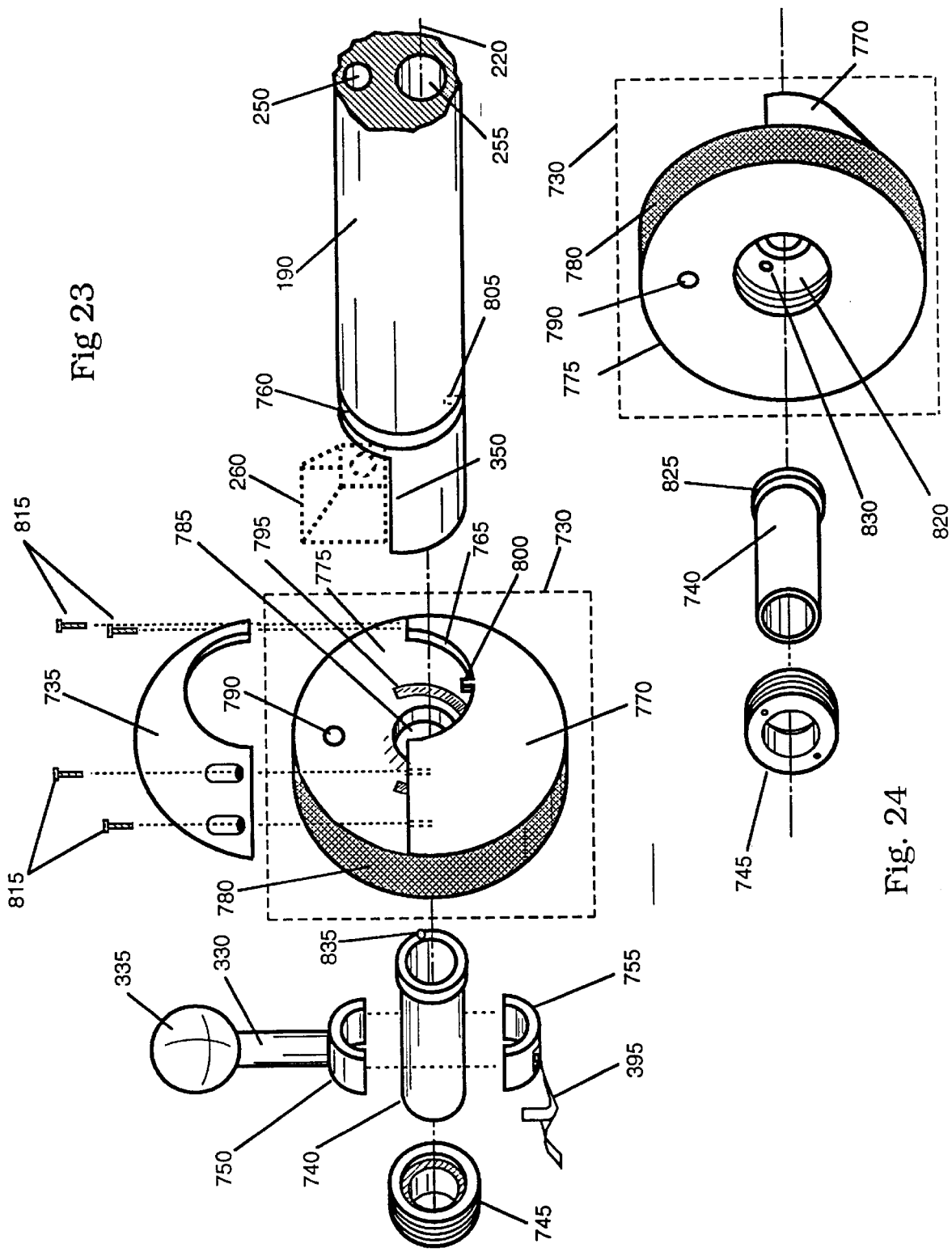

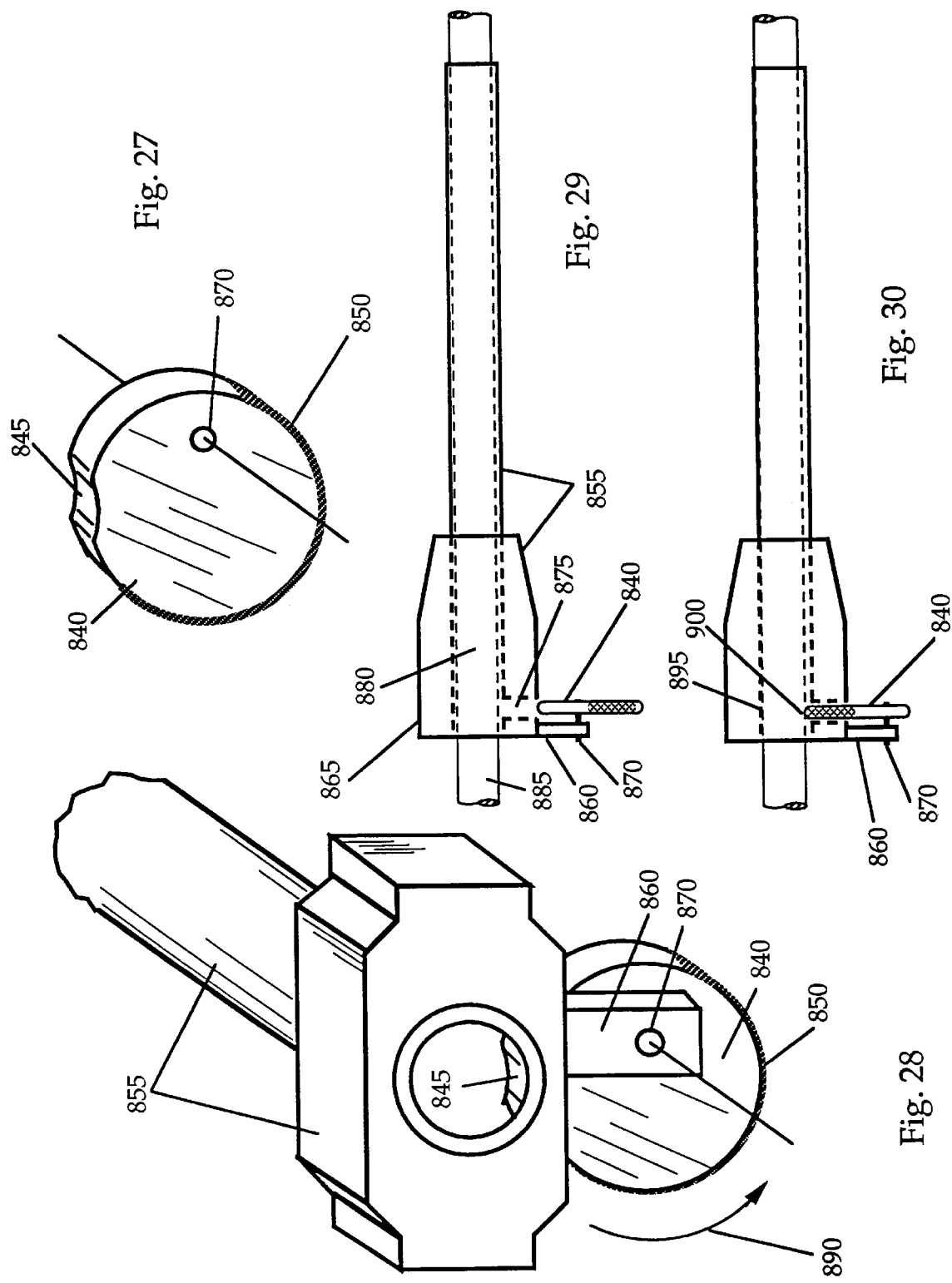

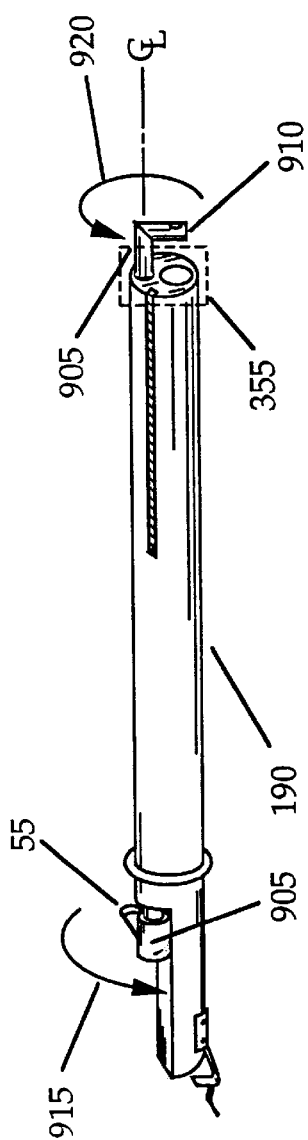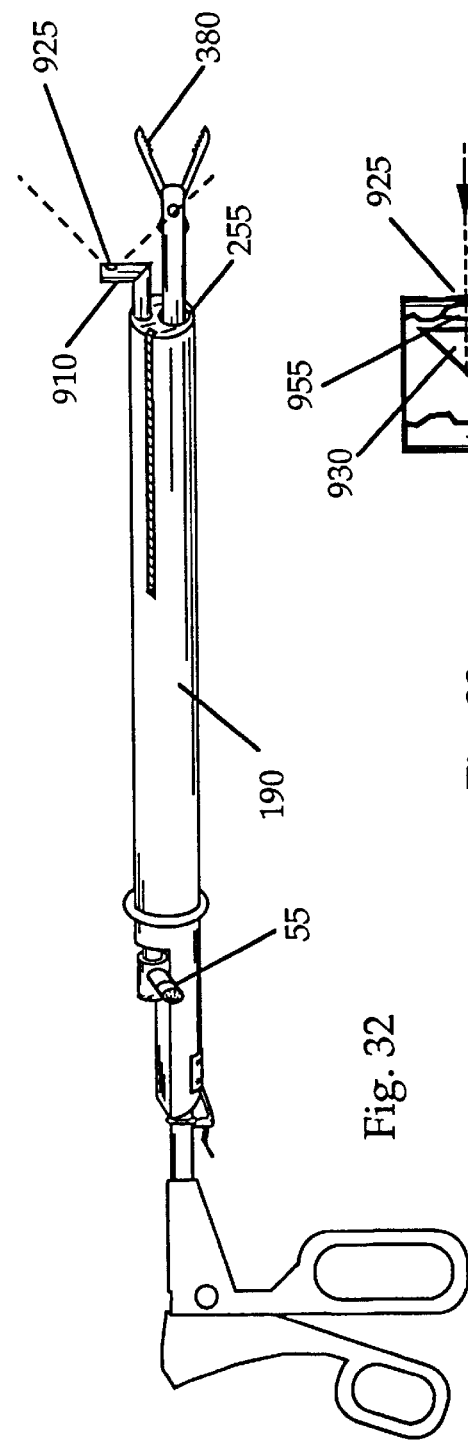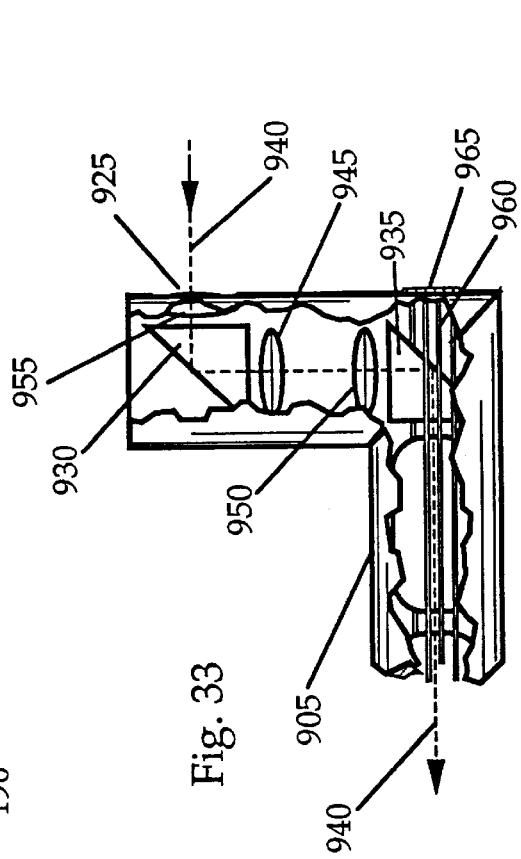

SYSTEM AND METHOD FOR ENDOSCOPIC IMAGING AND ENDOSURGERY

CROSS REFERENCE TO RELATED APPLICATION

This application is a continuation-in-part to U.S. patent application Ser. No. 08/841,167, filed Apr. 29, 1997, now U.S. Pat. No. 5,928,137 which is incorporated herein by reference in its entirety, which claims benefit of U.S. Provisional Application No. 60/016,830, filed May 3, 1996 and U.S. Provisional Application No. 60/021/559, filed Jul. 11, 1996.

BACKGROUND OF THE INVENTION

This invention relates to video endoscopy and to endosurgery, wherein endoscopy is understood to refer to all forms of medical endoscopy, including but not limited to laparoscopy, thoracoscopy, arthroscopy, gastroscopy, hysteroscopy, colonoscopy, and bronchoscopy, as well as to dental applications of endoscopy and to the use of endoscopic inspection instruments, such as borescopes, for non-medical applications, wherein video endoscopy refers to endoscopic visualization utilizing video acquisition and display of endoscopic images and wherein endosurgery refers to all surgical procedures performed under endoscopic visualization, including but not limited to tissue and organ repair, resection, implantation, and biopsy.

More specifically, this invention is related to a method and apparatus for improving manual dexterity in endoscopy and endosurgery by combining endoscopic, manipulative, video image forming, and video image display means in a novel manner that provides the surgeon or operator with improved hand-eye coordination.

The advantages of diagnosis and therapy performed under endoscopic visualization are well known. Such procedures are minimally invasive, result in shortened hospital stays, more rapid recovery, less cosmetic damage, and lower overall costs compared to conventional "open" procedures. However, most surgeons have much greater difficulty performing common surgical maneuvers using endbsurgical instruments (long-shafted graspers, scissors, etc. commonly used in endoscopic surgery) under endoscopic visualization. Whether the image is viewed by the surgeon with his eye to the eyepiece or, as is increasingly common, on a video monitor, the surgeon has poor hand-eye coordination compared to that of open surgery. The surgeon moves the instruments hesitantly and often inaccurately, whereas in open surgery the motion is rapid and precise. Simple routines, such as suturing and knot tying, are tedious and time consuming, even for highly skilled endoscopic surgeons. As a result, endoscopic procedures generally take more operating-room time than their open counterparts and are more exhausting for the surgeon. Moreover, many capable surgeons can not adequately master endoscopic technique; consequently, surgeries that potentially could be done endoscopically are still being performed as open procedures. In laparoscopic surgery, surgeons that operate with an instrument in each hand require the assistance of another surgeon to hold and direct the laparoscope, which increases the cost of the procedure. There is a need for new endoscopic surgery instruments and methods to overcome these limitations. The present invention addresses this need. It improves on prior-art endoscopic methods by providing the surgeon with greater hand-eye coordination by making endoscopic surgery look and feel more like open surgery.

In the discourse that follows, reference is made to "enhanced presence", which is defined below in connection with a special arrangement of a video endoscope, image display, and endosurgical instrument whereby the image of the distal tip of the endosurgical instrument is presented on a video display adjacent to the instrument handle and in a specific manner, along with the bodily tissues near the tip. The intent is to induce the surgeon to act as if the image of the tip, as seen in the display, is the tip itself. The reader will understand that the surgeon will not be actually deceived in this regard, but will, nevertheless, find it natural to respond as if he were. The surgeon will thus be led to instinctively use hand motions that are effective to accomplish endosurgical tasks, whereas with conventional endosurgical apparatus these motions are difficult to learn.

SUMMARY OF THE INVENTION

In accordance with the present invention, an endoscopic surgical system is provided for use in endoscopic surgery which includes an endosurgical instrument having an elongated shaft and an end-effector operably mounted to a distal end of the shaft. The endoscopic surgical system further includes a video endoscope device having an elongated telescope portion containing a distal viewing face, and a coupling device coupling the instrument to the endoscope device. This coupling substantially maintains the relative position of the elongated shaft adjacent the telescope portion such that the endoscope viewing face is rearward of the distal end effector to view the distal end-effector from a position along the shaft. A handle portion is operably coupled to the coupling device which enables the distal end-effector and the viewing face to be manually positioned as a single unit during endoscopic surgery. The handle portion is further configured to manually operate the end-effector. A video display device is operably coupled to the coupling device at a viewing angle and location therealong wherein an image of the end-effector displayed on the display device appears to be a substantially direct view of the end-effector that is positioned in-line with the insertion shaft.

In one aspect of the present invention, the handle portion is integrally formed with the endosurgical instrument, and the securing device is adapted to rigidly mount the handle portion to the instrument shaft. The coupling device includes a pair of opposed securing elements formed to releasably engage the handle portion and the telescope portion therebetween.

In another aspect, an adapter device is provided at a distal portion of the telescope portion of the endoscope which includes a bore portion formed and dimensioned for receipt of the instrument elongated shaft therethrough. This arrangement enables alignment of the end-effector in the field of view of the distal viewing end. A guide tube axially communicates with the bore portion for guided insertion of the elongated shaft through the guide tube and into the bore portion.

In another configuration of the present invention, the coupling device is configured to position the elongated shaft substantially parallel to adjacent the telescope portion, and is integrally formed with the handle portion. The integral handle portion and coupling device includes a bore formed and dimensioned for receipt of the instrument elongated shaft therein. A latch assembly releasably mounts the instrument to the handle portion between an unlatched condition, enabling removal of the elongated shaft from the bore, and a latched condition, releasably latching the instrument to the handle portion.

In yet another aspect, a linkage assembly operably couples the end-effector of the instrument to an actuation device of the handle portion for actuation of the end-effector when the latch assembly is moved to the latched condition. The linkage assembly includes an actuation rod disposed longitudinally along the elongated shaft which is coupled to the end-effector for movement between a first position and a second position. The linkage assembly further includes a boss member coupled to the actuation rod which operably engages the actuation device when the instrument is moved from the unlatched condition to the latched condition.

In another embodiment, a video endoscope system is provided for use by a surgeon in endoscopic surgery. The system includes a surgical instrument having an elongated shaft and an end-effector, and an elongated endoscope device including a telescope portion having a distal viewing face. A coupling device securably couples the instrument to the endoscope device in a manner substantially maintaining the relative position of the elongated shaft adjacent the telescope portion to facilitate viewing of the end-effector of the surgical instrument by the viewing face. A video display is mounted to the coupling device and adapted to display an image of the end-effector viewed by the distal viewing face. In accordance with this aspect of the present invention, a handle portion is operably coupled to the surgical instrument for actuation of the end effector, and is rigidly coupled to the coupling device for simultaneous positioning of end-effector and the endoscope viewing face as a unit. This movement is performed independent of the operation of the end-effector and in a manner substantially maintaining the end-effector in the field of view of the viewing face during operation and manipulation of the handle. By viewing the display, a surgeon operating the endoscope system by the handle will view and perceive the image of the end-effector on the video display as being directly viewed at a true position of the end-effector from the perspective of the surgeon. This enables the surgeon to effectively perform remote surgery with the hand-eye coordination approximating that of open surgery.

In still another aspect of the present invention, a method of performing endoscopic surgery is provided comprising the steps of: providing an endosurgical instrument having an elongated shaft and an end-effector operably mounted to a distal end of the shaft; and providing a video endoscope device having an elongated telescope portion containing a distal viewing face. The present inventive method further includes the step of coupling the endosurgical instrument to the endoscope device through a coupling device which substantial maintains the relative position of the elongated shaft adjacent the telescope portion such that the endoscope viewing face is rearward of the distal end effector to view the distal end-effector from a position along the shaft. The next steps includes inserting the end-effector and the distal viewing face simultaneously into a body part through a natural orifice or incision; and displaying an image of the end effector from the endoscope distal view face on a video display coupled to the coupling device. The method further includes the step of operating a handle portion operably coupled to the surgical instrument for actuation of the end effector, and rigidly coupled to the coupling device for simultaneous positioning of end-effector and the endoscope viewing face as a unit.

BRIEF DESCRIPTION OF THE DRAWINGS

FIG. 8 is a perspective drawing of the endoscopic surgery system depicted in FIG. 6.

FIG. 9 is a partial perspective drawing of a cannula for use with the endoscopic surgical system of FIG. 8.

FIG. 10 is a drawing of an endosurgical instrument such as is used in laparoscopic surgery, modified for use with the endoscopic surgery system depicted in FIG. 8.

FIG. 11 is a perspective drawing of an endoscopic telescope and a video camera head with partial mounting means for a video display, which are combined for use in the endoscopic surgery system depicted in FIG. 8.

FIG. 12 is a perspective drawing of a flat panel video display and partial mounting means for use in the endoscopic surgery system depicted in FIG. 8.

FIG. 13 is a perspective drawing of an insertion tube which is combined with the endoscope, camera head, and display for use in the endoscopic surgery system depicted in FIG. 8.

FIG. 14 is a perspective, cut-away detail drawing of the video camera head of FIG. 11.

FIG. 15 is a perspective detail drawing of a portion of the insertion tube of FIG. 13, showing the instrument retainer clip and the instrument bore seal.

FIG. 16 is a side view of the proximal end of the insertion tube showing the instrument retainer clip and the flapper valve.

FIG. 18 is a perspective drawing of an endosurgical instrument for use with the endoscopic surgery system of FIG. 17.

FIG. 19 is a perspective drawing of the basic assembly of the endoscopic surgery system of FIG. 17.

FIG. 20 is a perspective, cut-away detail drawing of the endosurgical instrument of FIG. 18 and the actuation means for operating said instrument.

FIG. 21 is a perspective, cut-away detail drawing of a portion of the basic assembly of FIG. 19.

FIG. 23 is an exploded, perspective, distal-end view of a system for switching the endoscopic surgery system between the configurations of FIG. 8 and FIG. 22.

FIG. 24 is a partial, exploded, perspective view of the system of FIG. 23, as seen from the proximal end.

FIG. 27 is a perspective view of a thumb-wheel cam for use in a medical cannula.

FIG. 28 is a perspective view of the distal end of a medical cannula incorporating the thumb-wheel cam of FIG. 27, which enables releasably locking in place an instrument inserted in the cannula.

FIG. 29 is a is a side view of the medical cannula of FIG. 28 with an instrument shaft within the cannula, showing the thumb-wheel cam in a disengaged position.

FIG. 30 is a is a side view of the medical cannula of FIG. 28 with an instrument shaft within the cannula, showing the thumb-wheel cam in the engaged position, pressing the shaft of the instrument against the opposite wall of the bore of the cannula.

FIG. 31 is a perspective view of the insertion tube of FIG. 8, wherein is housed an endoscope having a periscopic distal end.

FIG. 32 shows the insertion tube and endoscope of FIG. 31, with the endoscope rotated 180° from its orientation in FIG. 31, so as to provided an elevated perspective of the tip of a surgical instrument inserted through its bore within the insertion tube.

FIG. 33 is a cut-away view of the periscopic distal end of the endoscope of FIGS. 31 and 32, showing prisms and lenses that redirect the optical path and focus the image from the entrance pupil to the endoscope axis.

FIG. 36a is a side elevation view of an endoscopic surgery system comprising an operating endoscope, a flexible-shaft endosurgical instrument received within the endoscope, a video display, and a securing device for securing and registering the instrument's handle with respect to the endoscope and for attaching the display to the endoscope.

FIG. 36b is an enlarged, fragmentary, side elevation view of a distal portion of the endoscope's insertion tube of FIG. 36a.

FIG. 36c is a front elevation view of a distal end of the insertion tube of FIG. 36b.

FIG. 37 is a detailed exploded view of a securing device of the endoscopic surgery system FIG. 36a.

DESCRIPTION OF THE INVENTION

Figure 1:
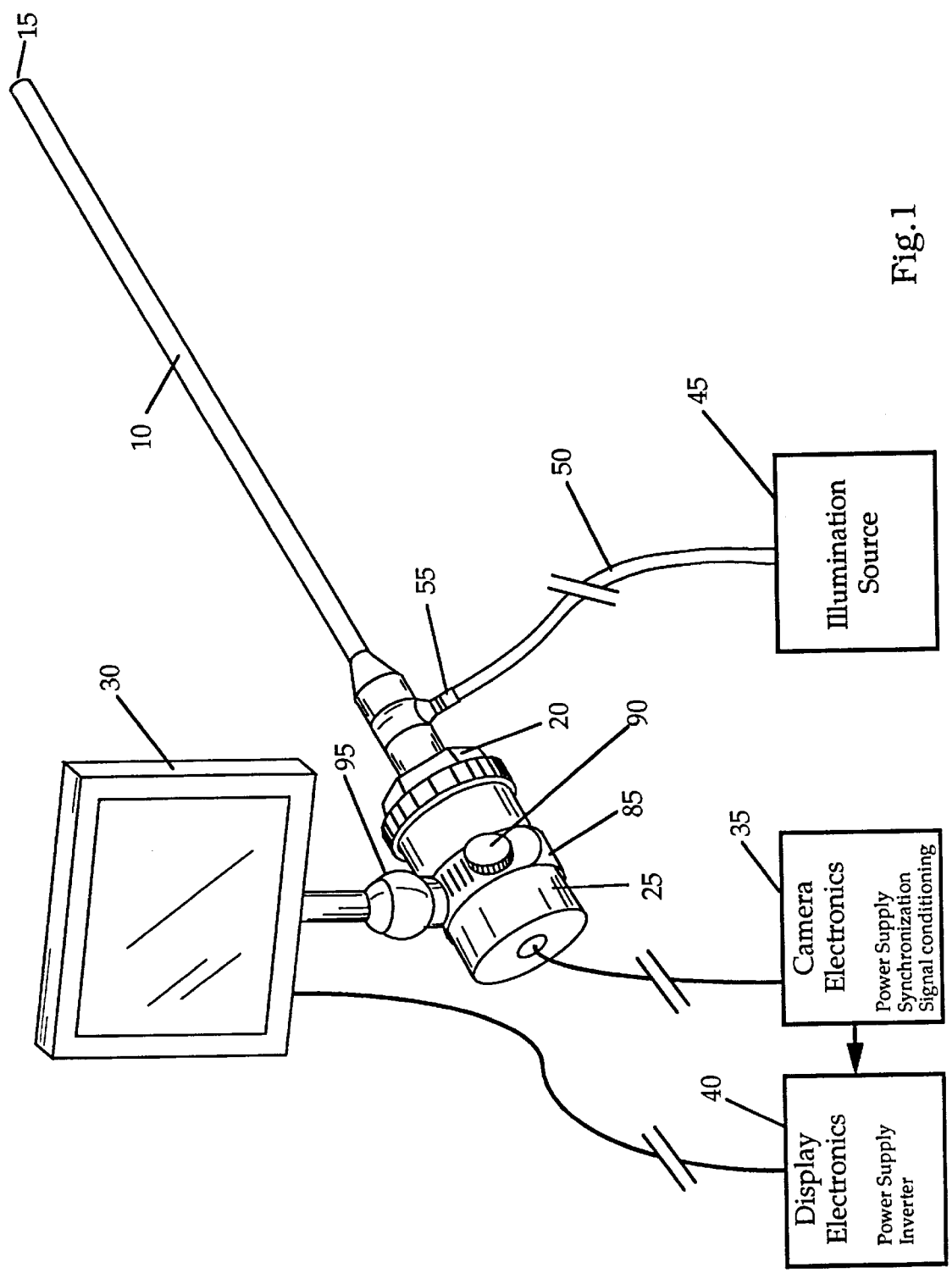
FIG. 1 is a perspective and schematic drawing of an endoscopic viewing system comprising a video endoscope with video display means releasably attached thereto, video signal processing means, and illumination means.

FIG. 1 shows a video endoscope comprising an elongated cylindrical tube 10 containing optical components that relay the images of the worksite from the distal end 15 of the endoscope to the eyepiece 20, and a video camera head 25, affixed to said eyepiece, which provides video signals corresponding to the endoscopic images. In current endoscopic practice, the video image is usually displayed on a large, cathode-ray-tube monitor, one to two meters from the endoscopist. According to the present invention, the image is presented on a video display means 30, such as a flat panel display, which, in this embodiment, is releasably attached to the camera head. The camera electronics unit 35 and display electronics unit 40 provide signal conditioning and synchronization and supply electrical power. An illumination source 45 provides light, which is conducted through a fiber-optic cable 50 to the endoscope's optical connector 55.

Figure 2:
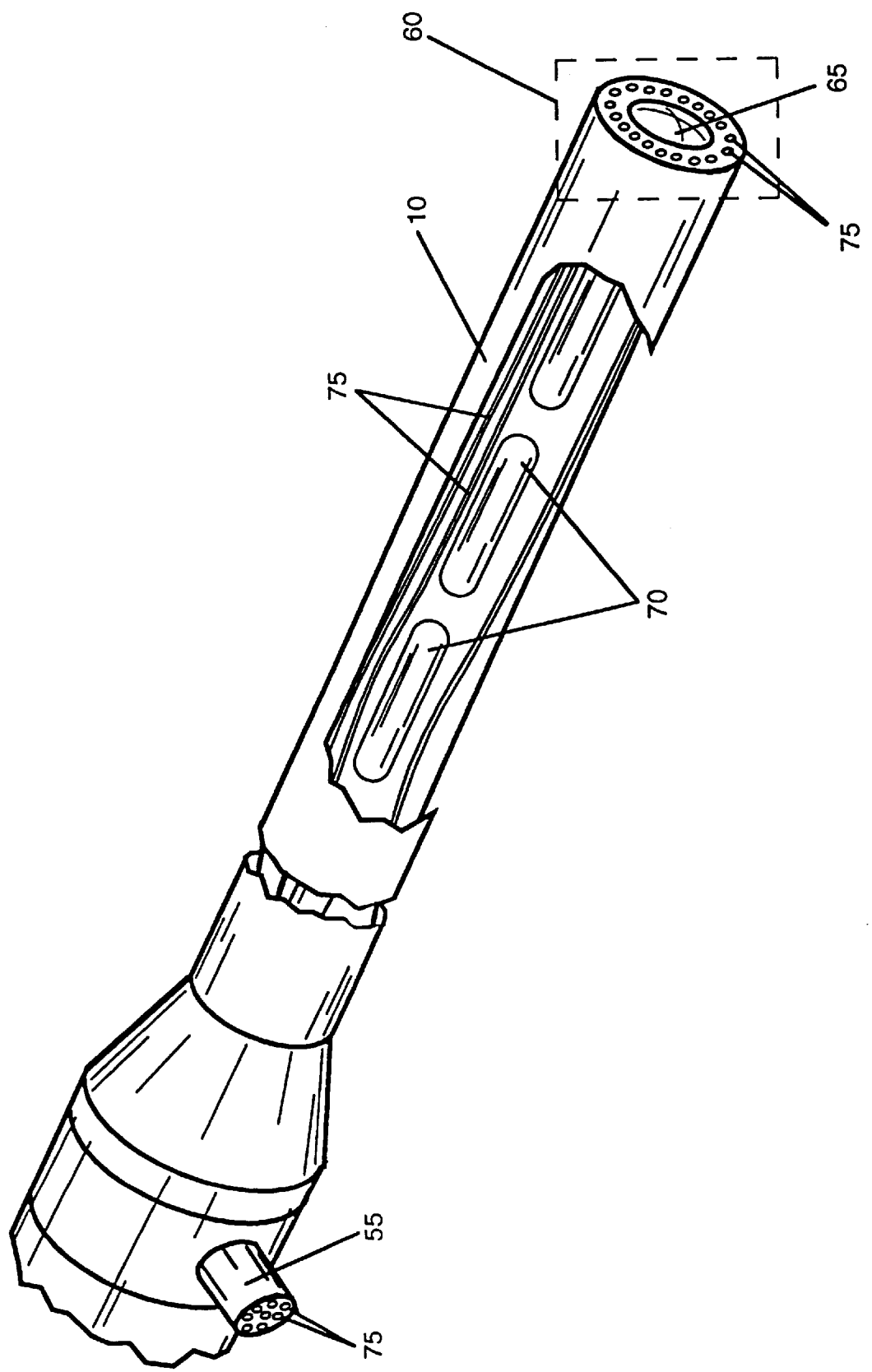
FIG. 2 is a cut-away perspective drawing of the distal portion of the FIG. 1 endoscope, showing the imaging rod lenses and the optical fibers that conduct the illumination from the optical connector to the distal face of the instrument.

FIG. 2 is a cut-away view of a portion of the endoscope of FIG. 1, including the elongated cylindrical tube 10, the distal face 60, the objective lens 65, the internal rod lenses 70, which conduct the image field from the objective lens to the eyepiece, and a plurality of optical fibers 75, which conduct light from the optical connector 55 and which terminate on the endoscope's distal face, from which said light radiates to illuminate the worksite. An example of such an endoscope is the Model 004378-901 laparoscope, manufactured by Cabot Medical Corp of Langhome, Pa. With reference again to FIG. 1, the light is supplied from the illumination source 45 to the optical connector 55 by means of the fiber-optic cable 50, which consists of a plurality of optical fibers within a flexible jacket. Endoscopic light source components suitable for this use are available, for example, from Circon-ACMI Inc. of Stamfort, Conn., as the model MV9082 Light Source and model MV8232 Fiber Light Guide, a fiber-optic cable with attached connector. Optical connectors of various designs are used by different manufacturers, and optical cables supplied with light sources generally are available with adapters to match the most commonly used endoscopes. Detachably affixed to the eyepiece 20 is a video camera head 25, which comprises a charge-coupled device (CCD) imaging array, a lens system, and a preamplifier, which is connected to the camera electronics unit 35, which contains power supplies, synchronization and digital addressing circuits, and signal conditioning circuits. The Circon-ACMI model 9660 camera head and camera electronics unit are suitable for this application.

In addition to the video endoscope system described above, video endoscopes of other designs also may be used in this invention, such as those with coherent optical fiber bundles instead of rod lenses, as described by Dorsey and Tabbs, with solid state image detectors located at their distal end, such as the model EVG-F from Fujinon, Inc., Scarsdale, N.Y., and with flexible rather than rigid, i.e., inflexible, tubes, e.g., the model P20 from Olympus Optical Company. Rigid endoscopes are endoscopes that can not be substantially deformed without damage to their internal optical elements. Flexible endoscopes include endoscopes with slightly bendable optics and thin metal walls, which are used in some arthroscopic procedures, and highly flexible endoscopes for the digestive tract and bronchi, which have soft plastic jackets. For medical use, these endoscopes are made in different sizes and shapes for a wide variety of diagnostic uses and for image-guided minimal-access surgery.

Referring again to FIG. 1., a video display means 30 is affixed to the endoscope, eyepiece, or camera head by a releasable mounting means, which permits the removal of the display means from the endoscope. The illustrated mounting means comprises a strap 85 of adjustable length and an adjustment knob 90 with which the strap can be shortened until it firmly grips the camera head. Conversely, the knob may be used to loosen the strap, enabling removal of the display. Detachability of the display may be desirable in medical endoscopy as it enables the endoscope to be autoclaved without damage to the display means, which may not endure high temperatures. The images produced by the video camera are viewed on the display means, enabling the endoscopist to see the image while directing his visual attention to the physical placement of the endoscope. The display 30 is adjustably attached to the mounting means by a ball and socket 95, with which the endoscopist may reposition the display for optimum viewing.

The display means 30 indicated in FIG. 1 preferably has a diagonal screen measurement of 70 mm to 120 mm, but may be any size that is convenient, and is light weight, for example, less than 50 gram. Although any video display may be used, a flat panel display (FPD) has certain weight and size advantages. By flat panel display is meant any means of video display that is thin compared to height and width and is lightweight compared to a conventional cathode-ray tube display. Flat panel displays include but are not limited to liquid crystal displays (LCD), field emission displays (FED), plasma displays (PD), and electroluminescent displays (ED).

The display may be entirely self contained, i.e., including within its housing all electronic circuits required to convert any standard video signal into a picture. It may even include batteries, such as does the Citizen model M329, available from CBM America Corp of Santa Monica, Calif. Alternatively, to reduce its size and weight, it may employ an external power supply and power inverter, situated in an external signal processing unit such as the display electronics unit 40 of FIG. 1. The Model LQ4NC01/02, manufactured by Sharp Electronics Corp., of Camas, Wash. is suitable for use in this manner.

Figure 3:
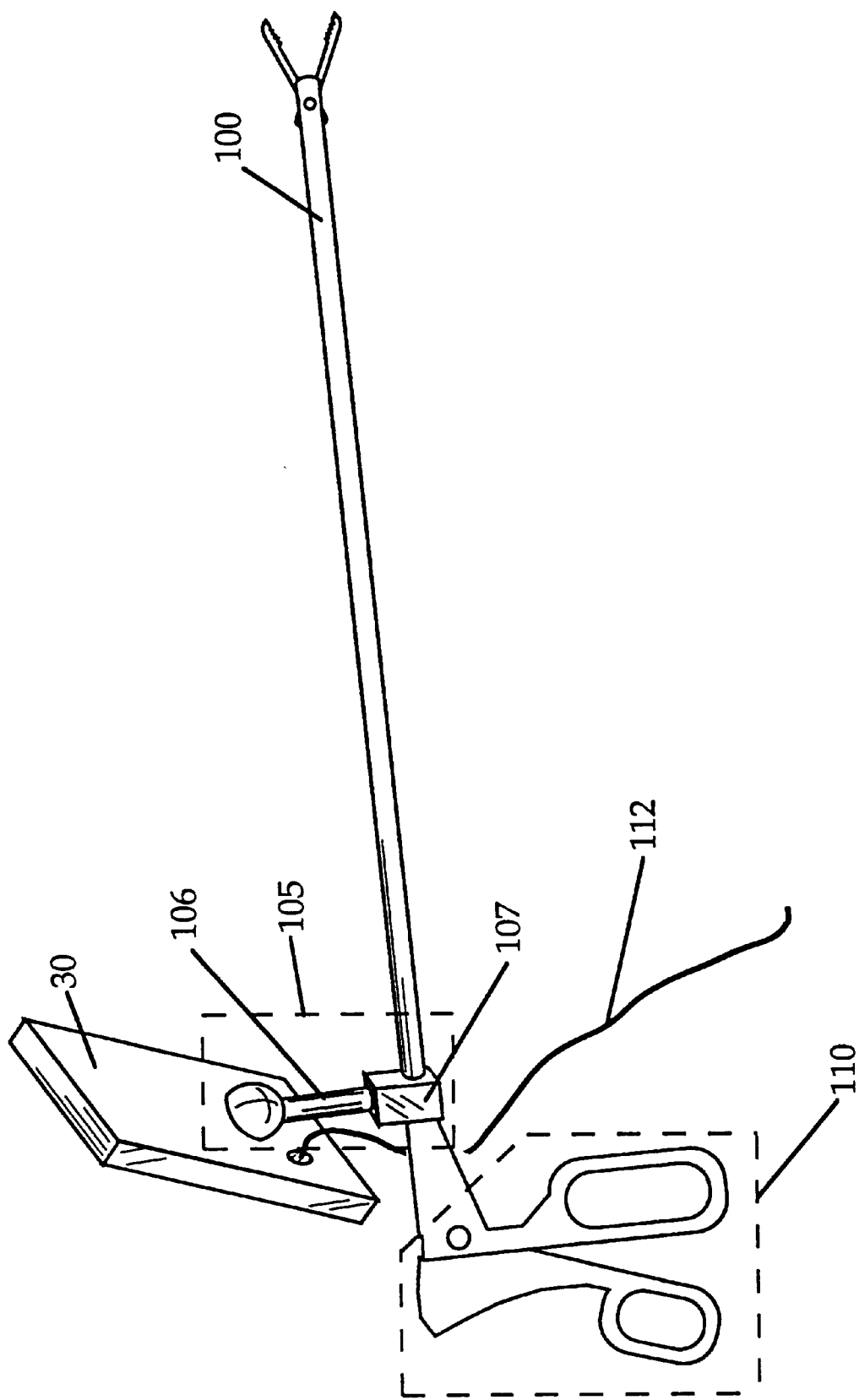
FIG. 3 is a perspective drawing of an endoscopic surgical instrument in combination with a video display means.
Figure 4:
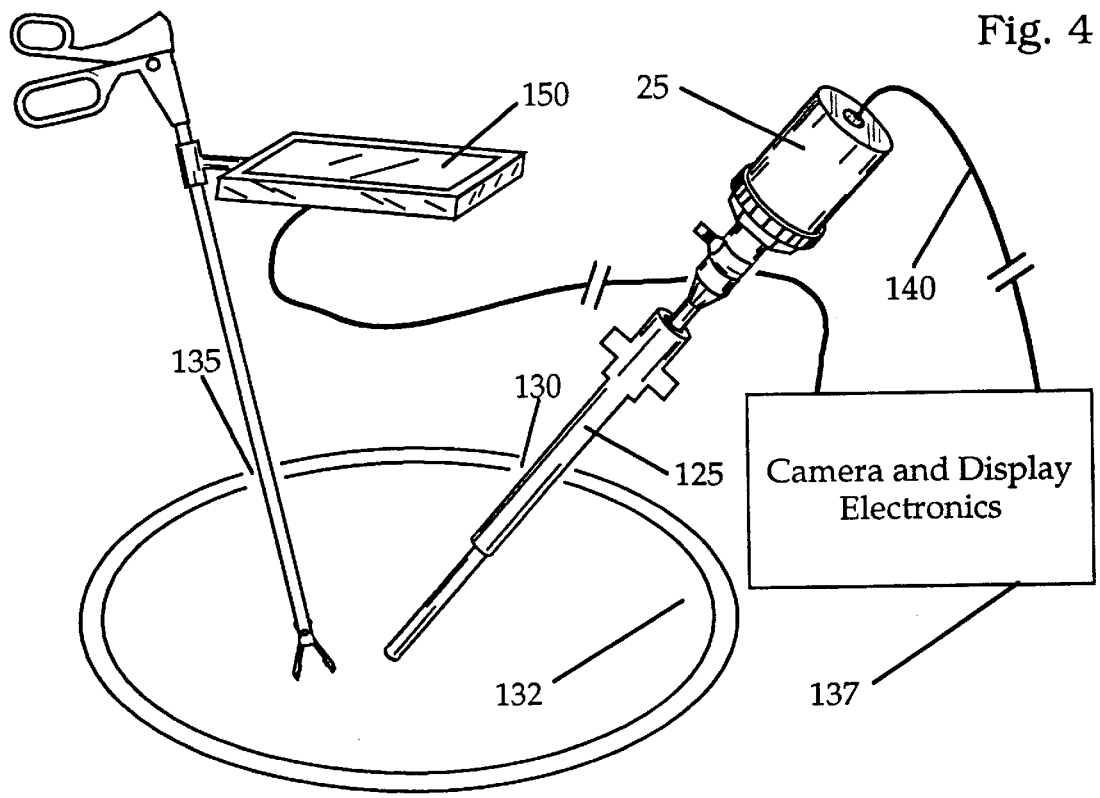
FIG. 4 is a perspective drawing and diagram of a system and method for endoscopic examination and surgery within a body, utilizing a video endoscope, an endoscopic surgical instrument separately disposed therewith, and a display means attached to said instrument, wherein the displayed image is derived from said video endo scope.

FIG. 3 shows an alternative embodiment of the present invention wherein a video display means 30 such as a flat panel display is affixed to an endoscopic surgical instrument with elongated shaft 100 with a mounting means 105 near its handle or hand-operated control means 110, enabling the surgeon to see the displayed image while directing his view toward the patient, his hand, and the instrument. The mounting means comprises a support stem 106 affixed to the back of the display, which is affixed to the top of a polymer or hard rubber block 107, through which the endosurgical instrument is passed, forming a releasable friction grip that holds the display in the selected position. Both instrument and display are adjustably secured by friction in their respective holes in the block. Video signals and electrical power to operate the display are supplied to the display through a cable 112, from electronic units, as described with reference to FIG. 1. Examples of endoscopic surgical instruments suitable for use in this embodiment are 5-mm-diameter laparoscopic instruments such as the Endo Grasp graspers, Endo Shears scissors, Endo Bowel clamps, and Endo Clip clip-appliers, which are manufactured by United States Surgical Corp. of Norwalk, Conn. With reference to FIG. 4, the image on the video display 150 is generated by a separate endoscope 120. The separate endoscope may be a conventional 10-mm diameter laparoscope such as is described above. The endoscope is inserted through a conventional trocar cannula 125, such as the Surgiport, manufactured by United States Surgical Corp., which passes through a first port 130 in the external surface 132 of the body part under examination. The distal end of the endoscopic surgical instrument is inserted through a second port 135 for the purpose of surgical manipulation within the field of view of the endoscope. The video signals from the video camera head 25 are conducted to the video camera electronics unit 137 through a first electrical cable 140 and thence through a second electrical cable 145 to the video display means 30.

Figure 5:
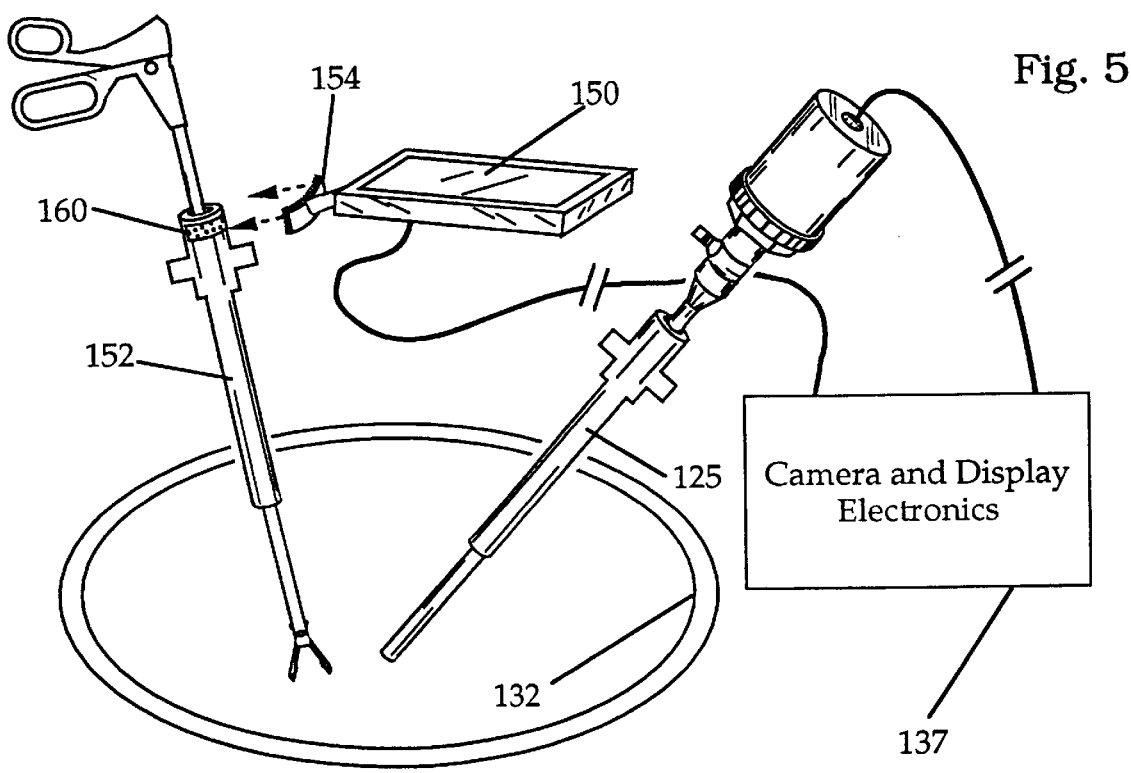
FIG. 5 shows a variation upon the system and method of FIG. 4 wherein the endoscopic instrument is introduced within the body through a cannula and the display is attached to the cannula rather than to the instrument.

FIG. 5 shows another embodiment of the present invention wherein the endoscopic surgical instrument is inserted into the body part by passage through a cannula 152, wherein the video display 150 is releasably affixed to the cannula by a mounting means comprising a support member 154, a Velcro strip 155, adhesively bonded to the support member, and a corresponding fabric anchoring strip 160 adhesively bound to the cannula. Materials for implementing this mode of attachment are commonly available. The display will be readily dismounted from the cannula before the cannula is sterilized or discarded.

Figures 6, 7:
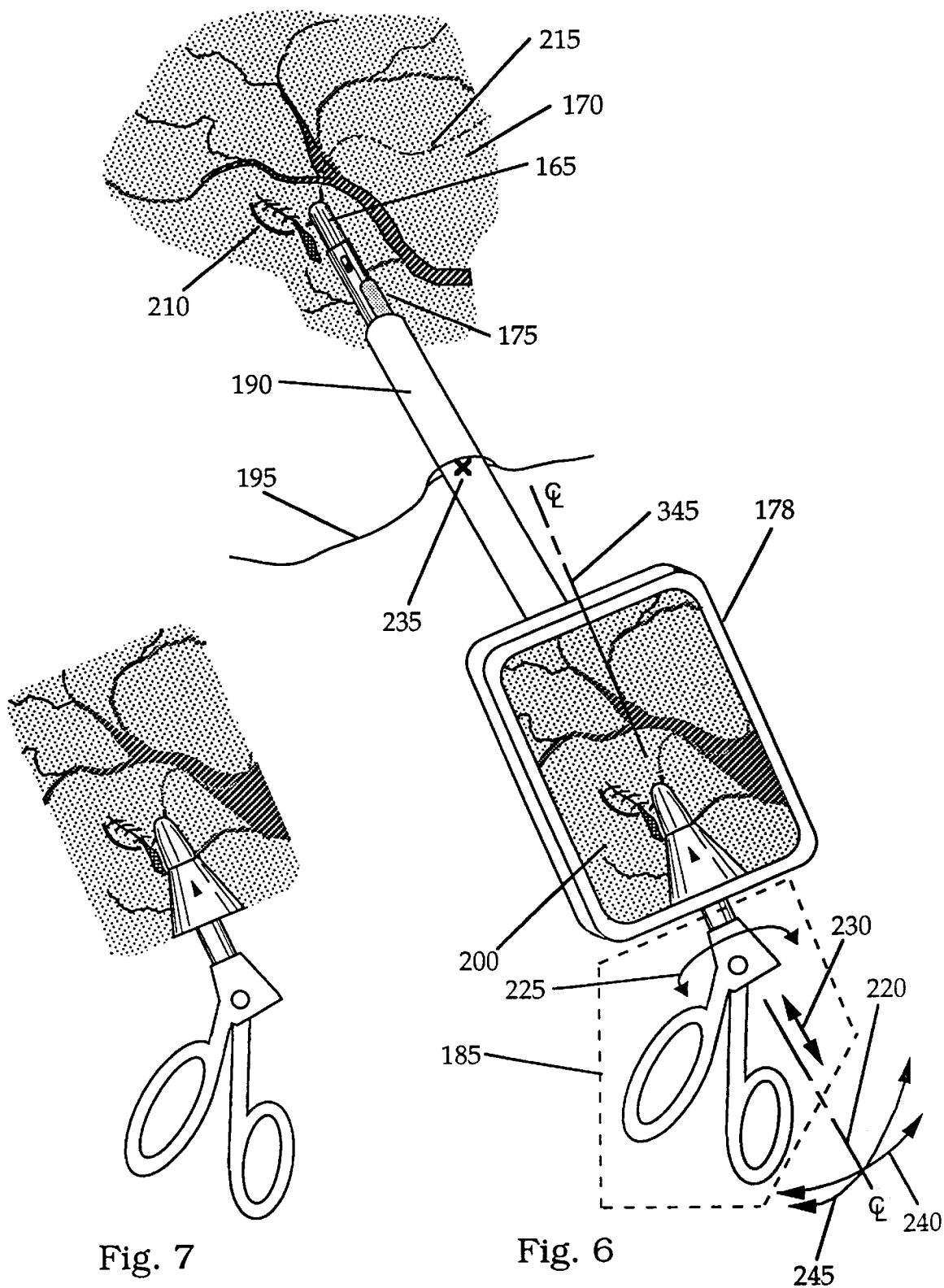
FIG. 6 is a perspective drawing of an endoscopic surgery embodiment of the present invention combining an endoscope, a video camera, a video display means, an endoscopic surgical instrument, and an insertion tube.
FIG. 7 is a rendering of the visual illusion created through use of the FIG. 6 embodiment, whereby the distal tip of the endoscopic surgical instrument, as observed in the video image, appears to be operably attached near the instrument handle, with the internal body tissues in the plane of the display.

FIGS. 6 through 16 illustrate another embodiment of the present invention. It is directed to making endoscopic surgical manipulation faster and more accurate by bringing the apparent position of the distal tip of the endoscopic surgical instrument and operative site close to the instrument handle, as it would be in open surgery, thereby improving hand-eye coordination. With reference to FIG. 6, this is achieved by generating a video image of the endosurgical instrument's distal tip 165 and of the operative site 170 from a video endoscope adjacent to and substantially parallel to said instrument, the distal tip 175 of said endoscope lying just proximal to the instrument tip 165 and presenting the said image on a video display 178, which display is located at a point just distal to the instrument handle or hand-operated control means 185. The endoscope's tube 10 (ref. FIG. 1) and the instrument shaft 100 (ref. FIG. 3) are enclosed in an insertion tube 190, which is passed through the external surface 195 of the body part under examination. In the case of abdominal surgery, generally, a trocar cannula is first inserted through the abdominal wall and the instrument or endoscope is passed through it, as depicted in FIG. 5.

Similarly, in the FIG. 6 embodiment, the insertion tube may enter the body through a cannula.

As FIG. 6 illustrates, the instrument handle is colocated with the image 200 of the instrument tip and tissues within the operative site are co-located. When looking at his hand and the instrument handle 185, the surgeon sees, in the same view, the image of the tip of the instrument, positioned as if it were extending immediately from the handle, and of the tissues and organs, which appear to be just beyond the nearby instrument tip. The surgical instrument depicted is a needle holder, such as the SzaboBerci Needle Driver, made by Karl Storz Endoscopy, Culver City, Calif. It is shown inserting a needle 210 with attached suture 215 through the tissue 170. This perception, depicted in FIG. 7, is familiar to all surgeons from their experience with open surgery.

As will become apparent through reference to FIGS. 6 through 16 below, the orientation of the image of the instrument tip is fixed with respect to the instrument shaft, owing to the fixed relationship between the instrument, the video endoscope, and the display. Referring again to FIG. 6, rotation of the instrument about its longitudinal axis 220, as indicated by arrow 225, causes the tip image to rotate about its axis in the display by the same degree. Advancing or withdrawing the instrument, as indicated by arrow 230, does not alter the positional relationship between the handle and the image of the tip, because the instrument, insertion tube, video endoscope, and video display move in and out as a single unit, as will become evident according to FIGS. 8 and 9 Again referring to FIG. 6, angular movement of the instrument handle about the fulcrum point 235 at the point of insertion through the abdominal wall, as indicated by the arrows 240 and 245, does not alter the relationship between the handle and the image if the tip. These fulcrum-constrained motions are identical to the motions that can be made in conventional laparoscopic surgery; however, with the present invention, the surgeon will be able to make them with more spontaneity and rapidity.

Attention is now directed to FIGS. 8 through 16, wherein a preferred embodiment of the conceptualization of FIG. 6 is depicted. FIG. 8 shows an assembled surgery system as would be used, for example, in laparoscopic surgery, with the omission of the separate camera electronics and display electronics units and the illumination source, these having been described in connection with FIG. 1. The mountable display is shown detached to indicate that the FIG. 8 embodiment can also be used without the attached display, by a surgeon viewing the image on a conventional monitor. The system comprises an insertion tube 190, an endoscope occupying a first longitudinal bore 250 in the insertion tube with its distal 175 end extending beyond the end of said tube, an endoscopic surgical instrument with its shaft 100 inserted through a second longitudinal bore 255 within the insertion tube, which bore is below the bore containing the endoscope, a video camera head 260 affixed to the proximal end 265 of the endoscope, a video display 178, a mounting assembly 270 for holding the video display in a position above the handle 275 of the instrument with adjustable orientation, an electrical cable 280 that carries power and video signals between the camera and display and the electronic processing unit, and a fiber-optic cable 50, which conducts the illumination energy from the illumination source to the optical connector 55 of the endoscope.

For purposes of maneuverability and ease of use, it is desirable to make the diameter of the insertion tube as small as is practical, consistent with the need to accommodate the endoscope and instrument. For example, an outer diameter of 10 mm or less would permit the insertion tube to pass through a standard 10-mm trocar cannula such as the 10-mm abdominal Surgiport, manufactured by United States Surgical Corp, depicted in FIG. 9 with a modification described below. It is desirable to use available endoscopic surgical instruments with shaft diameters of 5 mm. As construction materials and clearances will consume part of the remaining diameter, the available space restricts the endoscope diameter to be no more than 3 mm. Also, the endoscope must be long enough. The length of the shaft of a typical laparoscopic surgical instrument is about 330 mm. An endoscope length of 220 to 250 mm would satisfy this requirement. One endoscope with suitable dimensions is the bronchoscopic telescope Model 27018 A-C, manufactured by Karl Storz, which is 2.7 mm in diameter and 240 mm long. In this application, its eyepiece is replaced by a small video camera head coupled directly to the proximal end of the telescope portion. Referring now to FIGS. 11, 13, 14, and 15, the video camera head 260 comprises a housing 285 Which is releasably coupled to the endoscope by matching threaded ends 290 and 295, a charged-coupled-device (CCD) image sensor 300, a preamplifier 305, and a lens system 310 to focus the endoscopic image on to the image sensor. Modular CCD cameras suitable for this application, comprising small image sensor/preamplifier units and separate signal processing boards, are available, such as the model YH-7B20 camera from Sharp Corporation. As the endosurgical instrument channel is only a few millimeters away from the endoscope channel, there may not be sufficient radial clearance to center the image sensor on the endoscope axis 315. Accordingly, the lens system incorporates a prismatic element 320 that redirects the optical axis 325 away from the instrument channel. Alternatively, a mirror or internally reflective prism can be used to redirect the optical axis. Optical systems such as these are readily designed with existing lens-design software and are fabricated with stock optical components or with specially fabricated components, for which there are many suppliers in the optics industry, for example, Ferson Optics in Ocean Springs, Miss.

With reference to FIGS. 11 and 12, the adjustable mounting assembly 270 (ref. FIG. 8), by which the flat panel display 178 is attached to the video camera head 260, comprises a post 330 with attached metal ball 335 and an adjustable ball-retainer 340, attached to the display, by which the ball is held with sufficient friction to prevent unintended movement of the display. The orientation of the display may be readily adjusted by the endoscopist or surgeon for optimum viewing. With reference to FIG. 8 and particularly FIG. 6, the display may be perpendicular to the insertion tube or it may be inclined, as shown, with the top of the display rotated down toward the insertion tube. This will bring the axis 346 of the image of the instrument tip into closer alignment with the axis 220 of the instrument itself, strengthen the visual illusion that the image of the tip is connected coaxially with the instrument shaft. Individual surgeons may differ as to the most effective degree of tilt. As with any two-dimensional display of a three-dimensional field, there is directional ambiguity with regard to distances and motions. Inclining the display allows each user to minimize for himself the confusion caused by this ambiguity. In an alternative configuration of this embodiment, the display 178 and mounting assembly 270 are omitted and the surgeon views the image on a separate monitor, as discussed below with respect to FIG. 34.

With reference to FIGS. 13 and 15, the insertion tube 190 comprises a housing, made, for example, of plastic, approximately 250 mm in length. At its proximal end is a recessed plateau 350 which provides clearance for the video camera head. The endoscope, with camera attached, is inserted into the first bore 250 until it extends to or beyond the distal end 355 of the insertion tube by between 0 and 20 mm; it is secured therein by friction between the shaft and bore. The endoscope, camera head, and display may be removed from the insertion tube after use, so that they may be cleaned separately.

With reference to FIGS. 15 and 16, to limit the loss of insufflation gas when no instrument is in the instrument bore of the insertion tube, a flapper valve 360 (shown open) is provided within an enlarged portion 365 of the second bore 255. Such valves are in common use for the same purpose in trocar cannulas made by U.S. Surgical Corp. (referenced above.) Insertion of the instrument causes this valve to rotate up from its closed position 370 to its open position, as shown, clearing the bore for passage of the instrument. To limit the loss of insufflation gas during use of an instrument, a wiper seal 375 is provided at the proximal end of the instrument bore, comprising a flexible membrane with a hole slightly smaller than 5 mm. Such membrane seals are in common use for the same purpose in trocar cannulas made by U.S. Surgical Corp. (referenced above.)

With reference to FIG. 10, the instruments used in this embodiment are standard 5-mm laparoscopic surgery instruments, either reusable or disposable, such as the "Endo" series manufactured by United States Surgical Corp. and previously referenced herein. They comprise a hand-operated control means 275, a long hollow shaft 100, and end effector 380, and internal actuation means through which the hand-operated control means actuates the end effector. In the present invention these instruments are modified by the addition of a retainer ring 385, which is positioned and compressed to secure it around the shaft prior to use. With reference to FIGS. 8, 13, and 15, the purpose of the retainer ring is to ensure that during operation the instrument remains in the desired position along the instrument axis 220 with respect to the insertion tube. With reference to FIGS. 13, 15, and 16, the instrument is releasably locked in place by a spring-metal-mounted retaining latch 395 which engages retainer ring 385. When thus engaged, the distal tip of the end effector 380 of the instrument extends beyond the distal end 400 of the endoscope by a preselected distance, which is generally between 20 and 50 mm. Thereby, if the endoscope is of the "straight-ahead" type, i.e., the field of view is symmetrically disposed about the endoscope axis, then the instrument tip generally will occupy the central portion of the lower third of the endoscope's field of view, as depicted in FIG. 6. Once the latch is engaged, the instrument cannot move in or out, but it is free to rotate about its axis. The instrument may be released by a downward deflection of the retaining latch. It may then exchanged for another instrument without removing the insertion tube from the cannula.

In response to inward or outward force on the instrument handle, the insertion tube advances or withdraws within the cannula. With reference to FIGS. 8 and 9, the extent to which the insertion tube may be advanced is limited by the stop ring 405, which comes to rest against the proximal end 410 of the cannula at the point of greatest insertion. It is preferred that torque applied to the instrument handle to rotate the instrument about its axis does not induce rotation of the insertion tube within the cannula, as this would cause the display to rotate (it should be noted, however, that, because the endoscope and display would undergo the same rotation, the image of the tissues would not change in orientation.) With reference to FIGS. 8, 9 and 13, to ensure that the insertion tube does not rotate with respect to the cannula, a raised bar 415 is incorporated on the inside surface of the distal end 420 of the cannula and a mating grove 425 is made on the outside of the anterior portion the insertion tube, so that the grove and bar must be aligned for the distal end of the insertion tube to pass through the distal portion of the cannula. When grove and bar are engaged, the insertion tube is free to move in and out of the cannula but no relative rotation of the insertion tube and cannula is possible. The grove does not extend to the anterior portion of the insertion tube surface as this would interfere with the integrity of the contact between said surface and the round wiper seal 430 at the proximal end of the cannula, resulting in a leakage of insufflation gas.

To utilize this invention, according to the embodiment of FIGS. 8 through 16, for endoscopic visualization and surgery, the surgeon first places the cannula into the patient using well known endosurgical methods, such as those described by Phillips, et al. Then, the insertion tube, with the endoscope, camera head, and display attached thereto, is inserted into the cannula. An endoscopic surgical instrument is selected and inserted into the instrument bore of the insertion tube, engaging the retainer latch. The distal end of the instrument is now in position to execute a surgical maneuver on the internal tissues. The endoscopic image of the distal instrument tip and the tissues are visible in the display, just above the instrument handle.

Rotation of the instrument handle about the instrument axis causes the instrument to rotate within the insertion tube. The instrument tip is seen in the display to execute a corresponding rotation. Advancing and withdrawing the instrument handle causes the insertion tube to move in and out of the cannula, thereby, the image of the instrument tip remains always in the same position on the display screen. The visual perception provided by this embodiment, as illustrated in FIG. 7, is akin to that of open surgery-a short-handled instrument operating on tissue located near the surgeon's hand. Lateral motion of the instrument tip is produced in the customary laparoscopic mannerby rotating the instrument handle about the fulcrum that is established by the cannula at the point of insertion in the body part. It is within the scope of this invention to omit the attached display, in which circumstance the surgeon views the image on a conventional monitor. Although enhanced presence would not be provided, nevertheless, the surgeon may operate with an instrument in each hand, keeping the endoscope trained on the region of interest without conscious effort and without an assistant to direct the endoscope. This is further described below with respect to FIG. 35.

Figure 17:
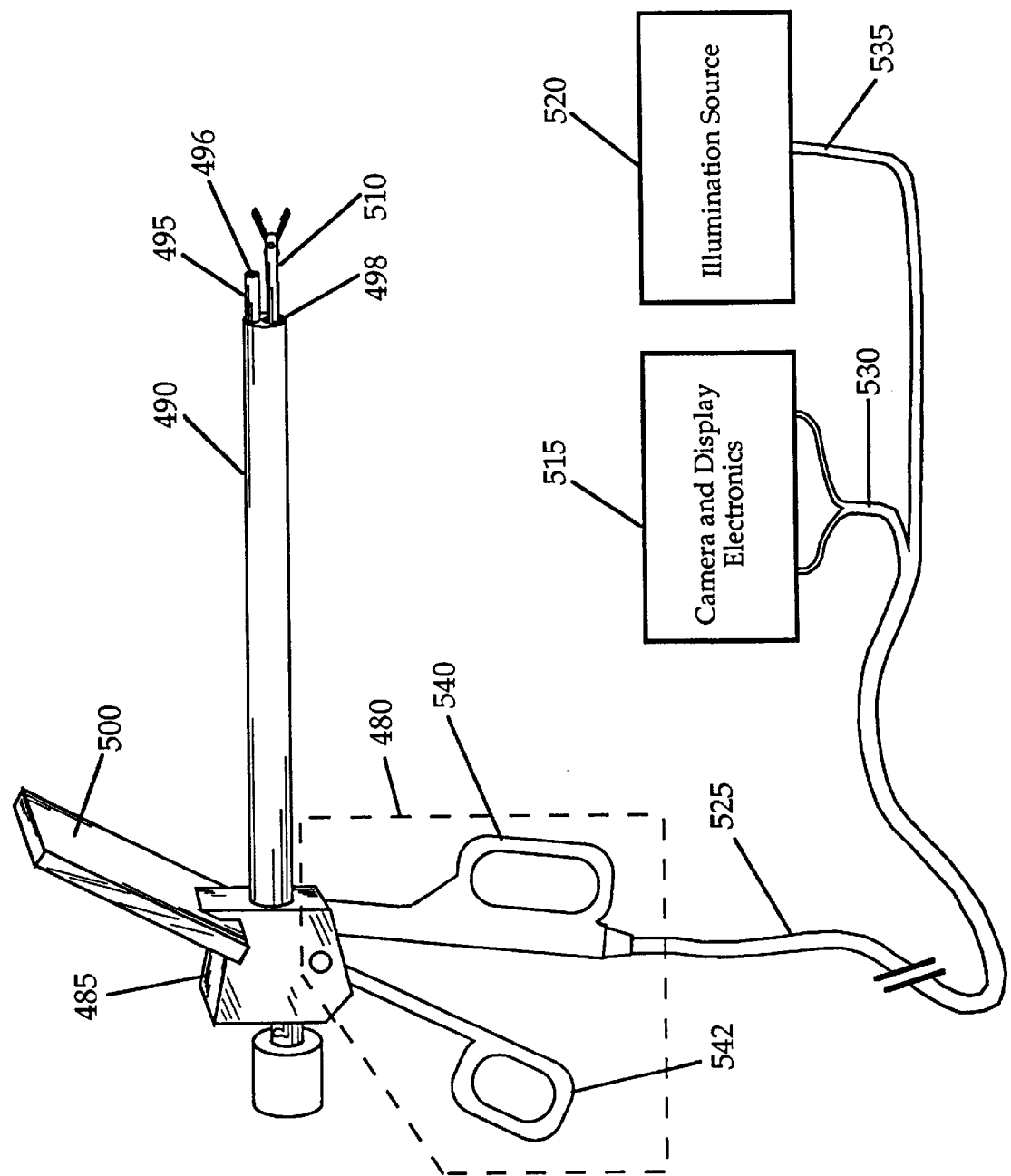
FIG. 17 is a perspective and schematic drawing of another embodiment of the present invention comprising an endoscopic surgery system wherein the hand operated controls are integrated with the insertion tube, camera, endoscope, and display, and interchangeable instruments are engaged by and operated by said controls.

Attention is now directed to FIGS. 17 through 21, which illustrate another embodiment of the present invention. With reference to FIGS. 17, 18, and 19, in this embodiment the hand-actuated controls 480 are combined with a body piece 485, insertion tube 490, endoscope 495, and display 500 to form a basic assembly, which, in combination with a compatible instrument 510, camera and display electronics unit 515, and an illumination source 520 form a complete endoscopic surgical system. In FIG. 17, the system is shown fully assembled and ready for operation, with an interchangeable instrument 510 inserted. A single cable 525, containing within it an electrical 530 and an optical 535 cable, is dressed through the forward member 540 of the hand-operated control means 480, which is affixed to the body piece 485 of the basic assembly. Said cable branches thereafter, with the electrical branch connecting to the camera and display electronics unit 515 and the optical branch connecting to illumination source 520. A rearward member 542, of the hand-operated controls 480 is pivotally mounted at pivot point 544 to the body piece 485 for the purpose of actuating the instrument, as described below.

FIGS. 18 through 21 illustrate certain details of the embodiment of FIG. 17. With reference to FIGS. 18 through 21, the interchangeable compatible instrument 510 comprises a cylindrical hollow shaft 545, an end-effector 550 (e.g., a grasper or scissors) comprising two operative elements 555 pivotally mounted to the shaft at a point 560 near the shaft's distal end, a hole 565 in each operative element proximal to the pivot point, a drive rod 570 located within the shaft and coupled to the operative elements by two short wires 575 each passing through the hole of one of the operative elements, a longitudinal slot 580 in one side of the shaft, a drive pin 585 affixed to the drive rod and extending through slot 580, a knob 590 on the proximal end of the shaft, and a twist-lock means immediately distal to the knob and concentric with the shaft 545, said twist-lock comprising a first cylinder 595 with a slot 600 on each side, said slots suitably shaped for releasably engaging opposing bayonets 605 (ref FIG. 21) projecting outward radially from a second cylinder 610 of smaller diameter, affixed to the proximal end of the body piece, which cylinder is concentric with the instrument bore 255 in the insertion tube 190.

With reference again to FIGS. 17 through 21, the endoscope 495, with the video camera head 260 attached to it, is mounted in the basic assembly 485 such that the distal, end 496 of the endoscope extends beyond the distal end 498 of the insertion tube by a distance suitable for the surgical use intended, which may be between 0 and 20 mm.

The optical fibers 620 that conduct light to the endoscope for field illumination originate at the illumination source, pass through the forward member 540 of the hand-operated control means, enter the endoscope through a light-sealed aperture 625, and continue to the distal face of the endoscope, where, as illustrated in FIG. 2, they terminate. With this configuration, the optical connector, such as the connector 55 of FIG. 2, which is used on prior art endoscopes, is eliminated, thereby reducing weight and increasing light transmission efficiency.

With reference to FIGS. 20 and 21, the rearward member 542 of the hand-operated control means is pivotally mounted to the body piece by the pivot axle 635 and extends above pivot point 544 to form an actuation means comprising a first and second "L"-shaped tines, 640 and 645 respectively, which lie below the aperture in the bore 650. Insertion of the instrument into the bore and clockwise rotation 655 of the instrument engages each bayonet 605 in the terminal detent 660 of its corresponding twist-lock slot 600 and rotates the drive pin 585 to a position between the tines 640 and 645. Alignment of the tines and the pin is ensured prior to insertion of the instrument by closing the hand control means; the operative elements of the instrument must be closed in order for the instrument to be inserted into its bore. Thenceforth, closure of the hand-operated control means causes the second tine 645 to apply a rearward pressure on the drive pin, which pulls the drive rod in a rearward direction, causing closure of the operative elements 555. Conversely, when the hand-operated control means is opened, the first tine 640 moves the drive rod forward, opening the operative elements. Counterclockwise rotation of the instrument disengages the bayonets 605 and causes the drive pin to swing clear of the tines and to be aligned with the slot 650 in the instrument bore 255, through which it passes when the instrument is removed or inserted.

The embodiment described in FIGS. 17 through 21 may be used with a cannula inserted through a body surface such as the abdominal wall, or may be used without a cannula, for example, when inserted through a natural orifice such as the mouth, nose, or rectum, or through an opening in the skin, for example, as in cosmetic or thoracoscopic endosurgery. Additionally, the embodiment of FIGS. 17 through 21 may be used without the attached display, in which circumstance the surgeon observes the image on a conventional monitor. Although enhanced presence is not provided in this mode, the surgeon benefits by operating the instrument and the endoscope with one hand.

Figure 22:
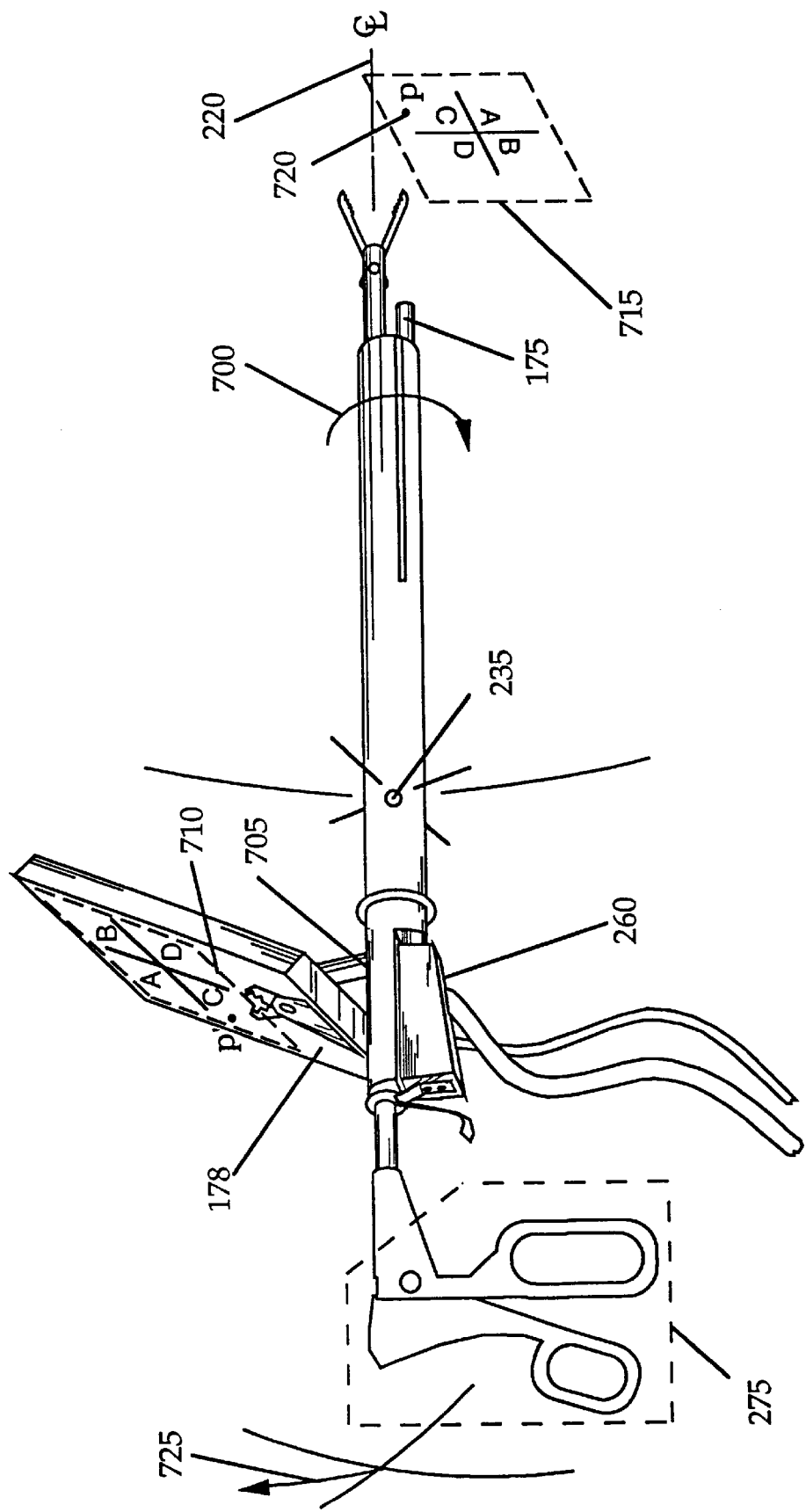
FIG. 22 is a perspective view of the endoscopic surgery system of FIG. 8 wherein the endoscope and video camera has been rotated about the axis of the endosurgical instrument, to a position beneath said instrument and an inverted orientation.

In FIG. 22 an embodiment of the present invention is disclosed which is directed to overcoming a well-known impediment of laparoscopic surgery-that operating through a port in the abdominal wall introduces a fulcrum at the insertion point 235, so that the instrument handle must be moved in the opposite direction of that which the instrument distal tip is desired to move. The FIG. 22 embodiment differs from that of FIGS. 6 and 8 in that the endoscope 175 and video camera head 260 are beneath the instrument rather than above it. This repositioning is achieved by rotating the insertion tube, endoscope, and camera head around the instrument axis 220 as a unit, as indicated by arrow 700. The display 178 is removed and reattached at a location 705 on the surface of the insertion tube opposite to that of the video camera head. In this embodiment, the image 710 of the distal instrument tip occupies the same position in the image field as in the FIG. 6 and 8 embodiment, however, the image of the object field is inverted, as indicated by object matrix ABCD 715 and its displayed image 710. Accordingly, to cause the image of the instrument tip to move toward a selected image point p' 720, the operator would move the instrument handle 275 generally toward that point in the display, as indicated by vector 725. The system is thereby caused to rotate about the fulcrum point, and the distal tip moves toward corresponding object point p 720, which is indicated in the display as movement toward p'. Thereby, reversal of instrument movement has been corrected and management of the instrument is now closer to that experienced in conventional open surgery, although the object field is inverted in the image.

With reference to FIGS. 23 and 24, a means is provided by which the embodiments of FIG. 8 and 22 can be combined in a single system, the mode of operation being selectable by the operator. The object is to provide for rotation about the instrument axis 220 of the insertion tube, endoscope, and camera as a single unit while maintaining the display in the upright position. With reference to the distal view of FIG. 23, this embodiment comprises an insertion tube 190 with endoscope and instrument bores 250 and 255 respectively, the proximal portion of which tube is indicated in the drawing, a coupling member 730, a coupling member cover 735, a proximal instrument tube 740, a threaded retainer ring 745, a first semicylindrical mounting element 750 to which is attached a post 330, with attached ball 335 for adjustably securing a display, if an attached display is used, and a second semicylindrical mounting element 755 to which is attached an instrument retaining latch 395.

The position of the video camera head 260 on the insertion tube is indicated in the drawing. Just distal to the recessed plateau 350 on which the camera head lies is a circumferential groove 760 which mates with the semicircular surface 765 at the distal end of the conical portion 770 of the coupling member 730. The coupling member comprises said conical portion and a proximal cylindrical portion 775, the circumferential surface 780 of which is knurled to provide a finger gripe for rotation of said member. A clearance bore 785 is provided through the cylindrical portion 775 for passage of the instrument. A second bore 790 is provided for passage of the camera's electrical cable. A semicircular groove 795 is provided in the distal face of the cylindrical portion, which mates with the proximal end of the insertion tube 190. A pin 800 is provided on the interior of the semicircular surface 765 which mates with a bore 805 within the circumferential groove 760 in the insertion tube to prevent rotation of the coupling member 730 with respect to the insertion tube 190. After insertion of the insertion tube into the coupling member, the coupling member cover 735 is secured into place with screws 815, thereby firmly securing the insertion tube against movement with respect to the coupling member.

Referring to FIGS. 23 and 24, the instrument tube 740, is inserted into the cylindrical recess 820 in the proximal face of the cylindrical portion 775 of the coupling member 730. The threaded retainer ring 745 is passed over the proximal insertion tube, which has an inner diameter less than that of the collet 825 of the instrument tube. The retainer ring is threaded into the cylindrical portion of the coupling member until it pressure the collet against the cylindrical portion of the coupling member with enough force to resist, but not prevent, rotation of the instrument tube in the cylindrical recess. A detent mechanism is provided by or more spherical pits 830 on the end surface of the cylindrical recess 820, radially positioned so as to nest with a spring-loaded spherical bead 835 affixed to the distal surface of instrument tube 740. The detent mechanism releasably secures the instrument tube at selected rotational positions. In particular, two diametrically opposed pits can be used to stabilize the system for operation in the modes of FIG. 8 and FIG. 22.

The semicylindrical mounting elements 750 and 755, which have inner diameters equal to the outer diameter of the instrument tube, are affixed to each other by screws or an adhesive, securing the instrument tube there-between.

Figure 25:
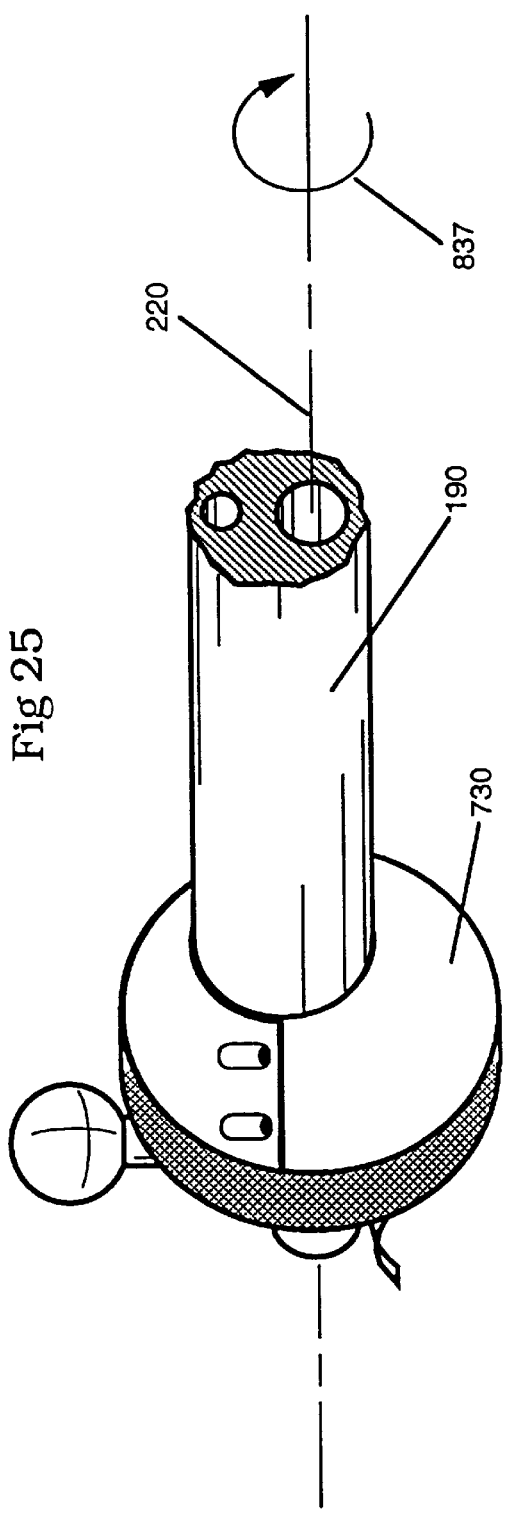
FIG. 25 is an assembled view of the part of the system of FIG. 23, with the endoscope bore positioned above the instrument bore.
Figure 26:
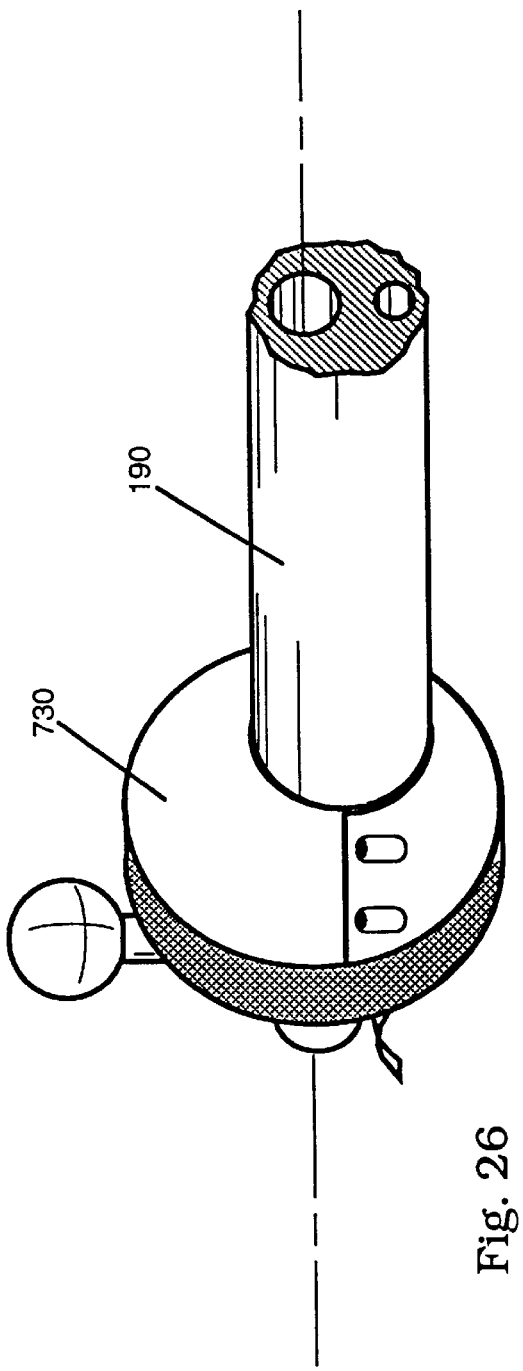
FIG. 26 is a partial assembled view of part of the system of FIG. 23, with the endoscope bore positioned below the instrument bore.

FIG. 25 illustrates the orientation of the coupling member 730 and insertion tube 190 for operation according to the mode of FIG. 8. Rotation of these elements about the instrument axis 220, as indicated by vector 837, converts the instrument to the mode of FIG. 22, which is depicted in FIG. 26. To change between operating modes, the operator grasps the instrument tube, display mount, or display with one hand and with the other hand grasps the knurled surface of the coupling member, rotating it one-half turn.

The embodiments illustrated in FIGS. 6, 8, and 22 through 26 provide for axially securing the instrument to the insertion tube by means of a retaining latch. Thereby, the endoscope, video camera, and display move in and out in synchrony with the advancement and withdrawal of the instrument. It is also within the scope of this invention to operate in a manner in which the endoscope, video camera, and display are fixed at a selected degree of insertion and the instrument, with the instrument latch disengaged or absent, is advanced and withdrawn independently. This may be effected by omitting the cannula of FIG. 9 and, as illustrated in FIG. 6, passing the insertion tube directly through a port made in the body wall. Alternatively, in another embodiment of this invention, a cannula, illustrated in FIGS. 27 through 30, is employed which provides for securing the insertion tube at any desired degree of insertion. FIG. 27 shows a thumbwheel/cam 840 comprising a disk with an eccentric axle 870, which disk is provided with a detent 845 and a roughened edge portion 850 that provides friction for finger operation. FIG. 28 shows a cannula 855, with the thumbwheel/cam 840 of FIG. 27 mounted thereon by a means of a post 860 affixed to the proximal end 865 of the cannula and an axle 870. FIG. 29 shows a side view of the cannula and thumbwheel/cam 840, post 860, and axle 870.

A slot 875 is provided in the wall of the cannula, which allows clear passage of the thumbwheel into the cannula bore 880. The thumbwheel/cam in shown in the disengaged position. A shaft 885, such as an insertion tube, is shown within the bore, the shaft being free to move within said bore. Rotation of the thumbwheel/cam, as indicated by vector 890 in FIG. 28, causes the thumb wheel/cam to enter the bore and press on the shaft at point 900, forcing it against the opposite wall of the bore at point 895, thereby preventing it from moving within the bore, as illustrated in FIG. 30. The detent 845 on the thumbwheel/cam prevents inadvertent release of the shaft.

FIGS. 31 through 33 illustrate another embodiment of the present invention wherein an elevated perspective is provided of the tip of a surgical instrument, for example an instrument inserted through the instrument bore of the embodiments of FIGS. 8 and 22. FIG. 31 shows an insertion tube 190 with endoscope 905. The endoscope is provided with a periscopic distal element 910. The endoscope, which may be rotated within its bore in the insertion tube, is shown, in FIG. 31, positioned so that periscopic distal element lies adjacent to the distal end 355 of the insertion tube, overlaying the instrument bore. The length of said periscopic distal element is selected so that it does not extend beyond the area of said distal face, thereby, it does not impede passage of the insertion tube through a cannula and into the body. After insertion, the endoscope is rotated one-half turn, which may be accomplished by grasping the optical connector 55 and turning it according to vectors 915 and 920.

Referring now to FIG. 32, after rotation of the endoscope the entrance pupil 925 of the endoscope is above the level of the insertion tube, affording an elevated perspective of the distal tip 380 of the instrument, which may now be inserted through the unblocked instrument bore 255 in the insertion tube.

FIG. 33 is a detailed cut-away view of the distal portion of the endoscope, showing the optical components therein. Prisms 930 and 935 redirect the optical axis 940 from the entrance pupil 925 to the main optical tube 905 of the endoscope. Lenses 945 and 950 refocus the image for transmission through the endoscope. The well known principles of endoscope design may be readily adapted to the design of this embodiment. The objective lens 955 is positioned at the entrance pupil. Illumination of the field of view is provided through optical fibers 960 which terminate in an illumination window 965 below the entrance pupil.

Figure 34:
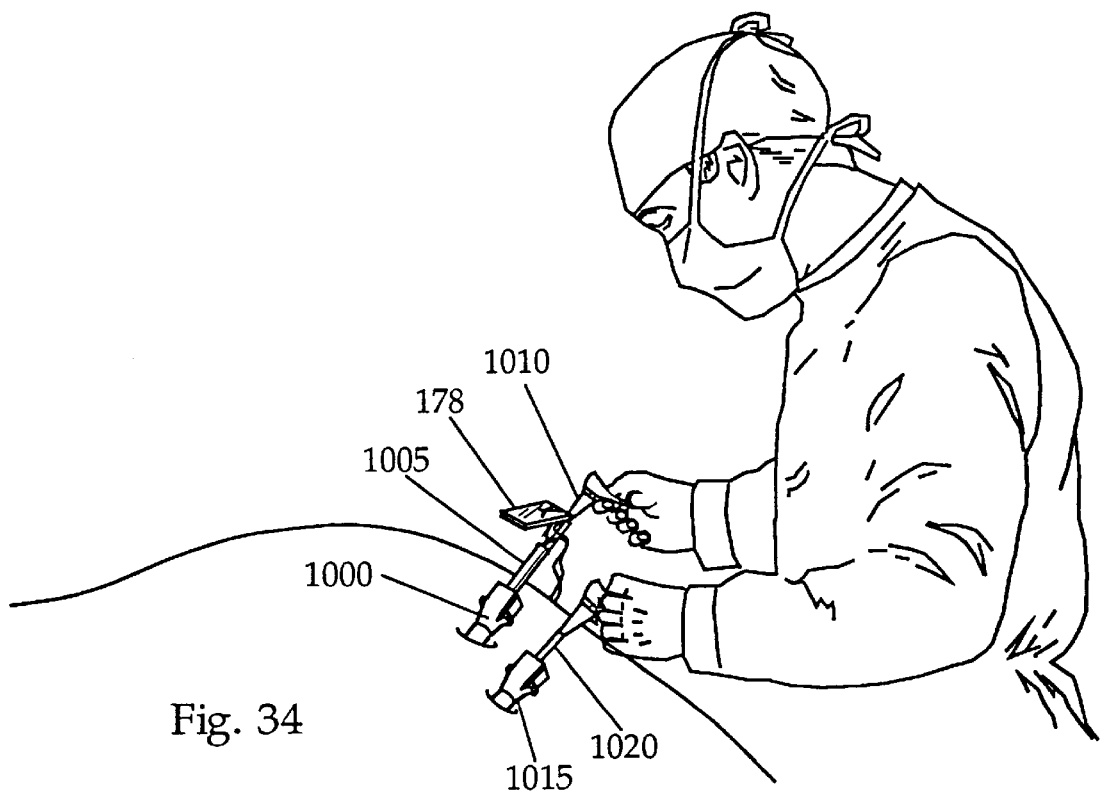
FIG. 34 depicts the endosurgical instrument, video endoscope, insertion tube, and cannula of FIGS. 8 through 13 used in combination with a video monitor by a surgeon operating with an instrument in each hand.

The embodiments of FIGS. 8 through 13 and 22 through 33 may be employed to carry out a laparoscopic surgical procedure with enhanced dexterity and enhanced presence. With reference to FIG. 34, the surgeon inserts the cannula of FIG. 9, here designated 1000, through the abdominal wall and then inserts therethrough the FIG. 8 embodiment of the present invention, here designated 1005. The surgeon then selects an instrument 1010 and inserts it through the instrument bore (255 of FIG. 8) until it is axially secured by the latch (395 of FIG. 8). If two handed surgery is contemplated, a second port is established with a cannula 1015 of conventional design and an instrument 1020 of conventional design is inserted therethrough. Other ports in the abdominal wall for instruments operated by other persons may be established as desired. The surgeon views the endoscopic image on display 178, which image shows the tip of instrument 1010, the adjacent tissues and the tip of instrument 1020 when it within the field of view.

Figure 35:
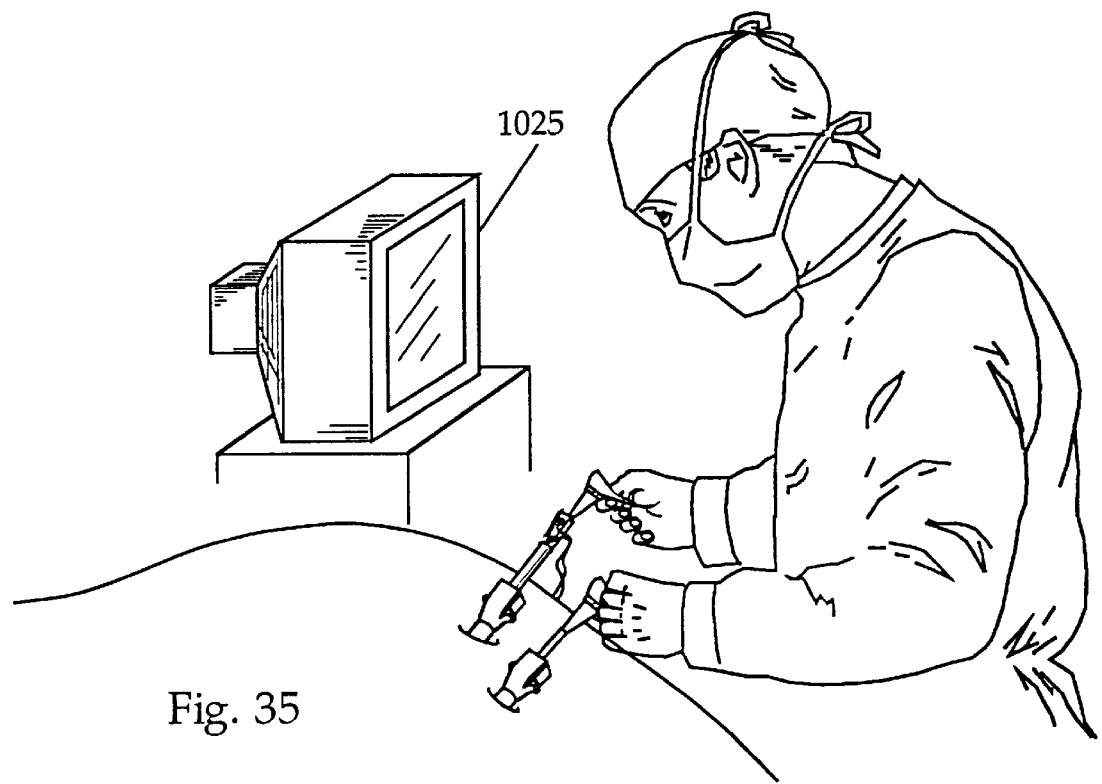
FIG. 35 depicts the endosurgical instrument, video endoscope, insertion tube, video display, and cannula of FIGS. 8 through 13 used in combination by a surgeon operating with an instrument in each hand.

With reference to FIG. 35, a laparoscopic surgical procedure can also be carried out with the display 178 removed, turned off, or ignored. Set up is the same as described with respect to FIG. 34, except that a separate monitor 1025 is provided in accordance with the prior art practice of laparoscopic surgery. Although enhance presence is not provided, this configuration does enable the surgeon to operate with an instrument in each hand while simultaneously, and without conscious effort, keeping the laparoscope directed at all times to the operating site.

FIG. 36a depicts another embodiment of the endosurgical system 1026 of the resent invention, which incorporates an operating endoscope 1028 having instrument ore 1060 through which an end effector 1075 of endosurgical instrument 1032 is passed. The jacket of the operating endoscope 1028 serves as the insertion tube by which the instrument and telescope are jointly introduced into a body part as a unit. One type of operating endoscope, as illustrated, is model 27015B Office Hysteroscope manufactured by the Karl Storz Company of Tuttlingen, Germany. However, other operating endoscopes designs may be used within the scope of the present invention as well.

The operating-endoscope portion of this embodiment of the present invention comprises elongated cylindrical sheath 1030, eyepiece 1035, mid-section 1040, and other optical components and elements described below with further reference to FIGS. 36a–36c. Within sheath 1030, optical elements 1080 relay the images of objects within the field of view 1085 to video camera head 1090.

The endosurgical instrument 1032 comprises a handle portion 1068, an elongated flexible shaft 1070, an end-effector 1075, and a drive rod 1078, through which operation of the handle is transmitted to the end-effector. Flexible shaft 1070 of the endosurgical instrument is preferably introduced into the instrument bore 1060 of the endoscope through ferrule 1045 and guide tube 1050. During insertion, the end effector 1075 and the flexible shaft 1070 pass through adapter 1055 which communicates with instrument bore 1060. The flexible shaft is then redirected so that end-effector and shaft emerge from the distal face of the endoscope.

In the preferred form, optical connector 1095 of FIG. 36a couples light from an external source to optical fibers 1100 of FIGS. 36b and 36c, which respectively are enlarged side- and front-views of telescope end-section 1105 of FIG. 36a. Referring to FIG. 36a, a flat-panel video display 1110 is positioned above the endoscope and secured thereto through a spherical joint 1115 or the like, which is attached to the back of video display 1110 by a short rod 1120. The spherical joint 1115 is adjustably clamped between the two opposed securing elements 1122, 1122' (FIG. 37) of a coupling or securing device 1125, which also receives and secures the stem 1128 of the distal finger-loop 1132 of instrument handle 1068. The opposed securing elements 1122, 1122' of securing device 1125 securely clasp cylindrical sheath 1030 and guide tube 1050 of the endoscope therebetween. By this means, the endosurgical instrument 1032 is secured against further insertion, against unintended withdrawal, and against rotation with respect to the endoscope. Thereby, using the instrument handle, the instrument and endoscope may be manipulated and operated as a single unit.

Figure 36:
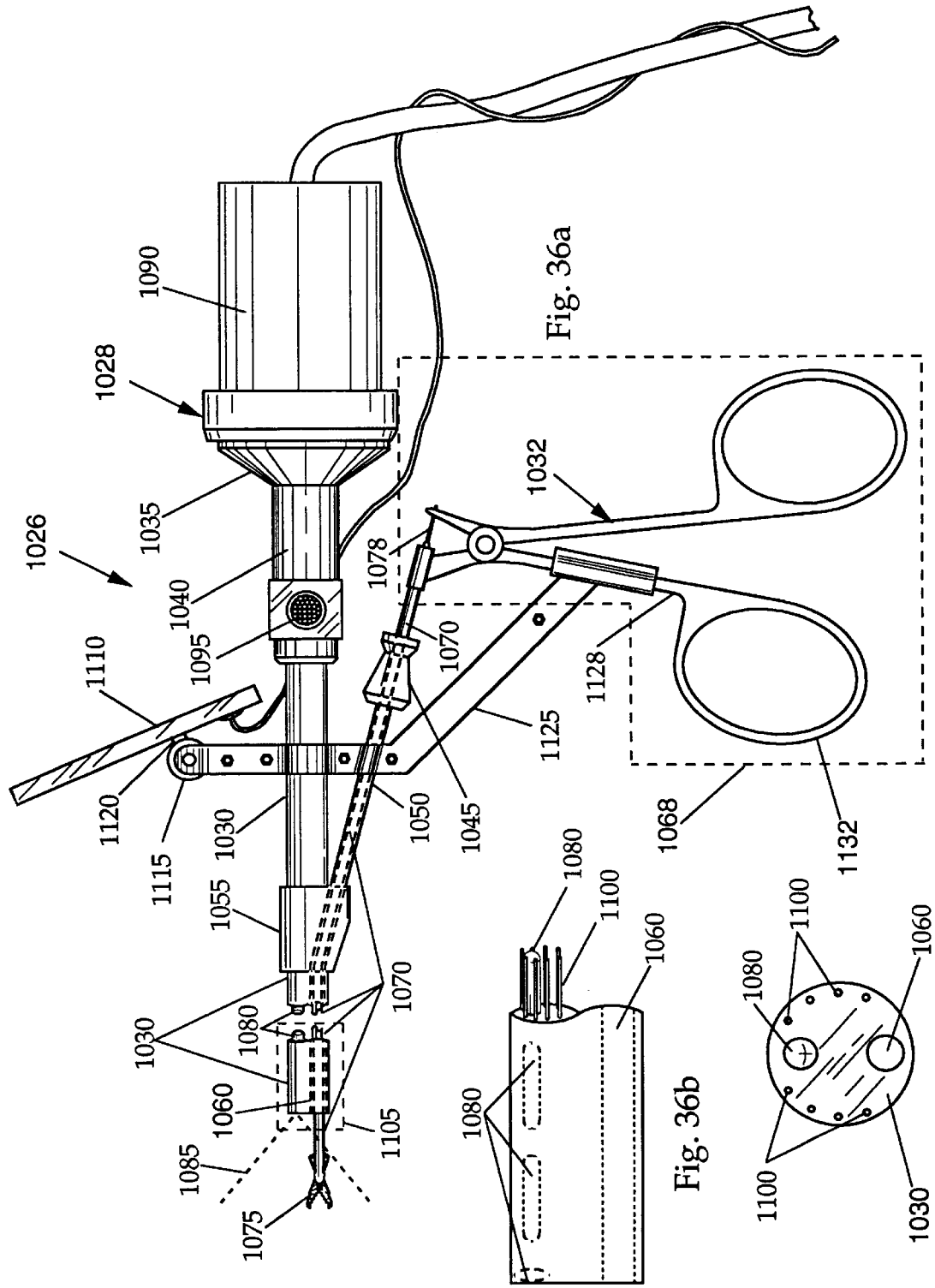
Figure 37:
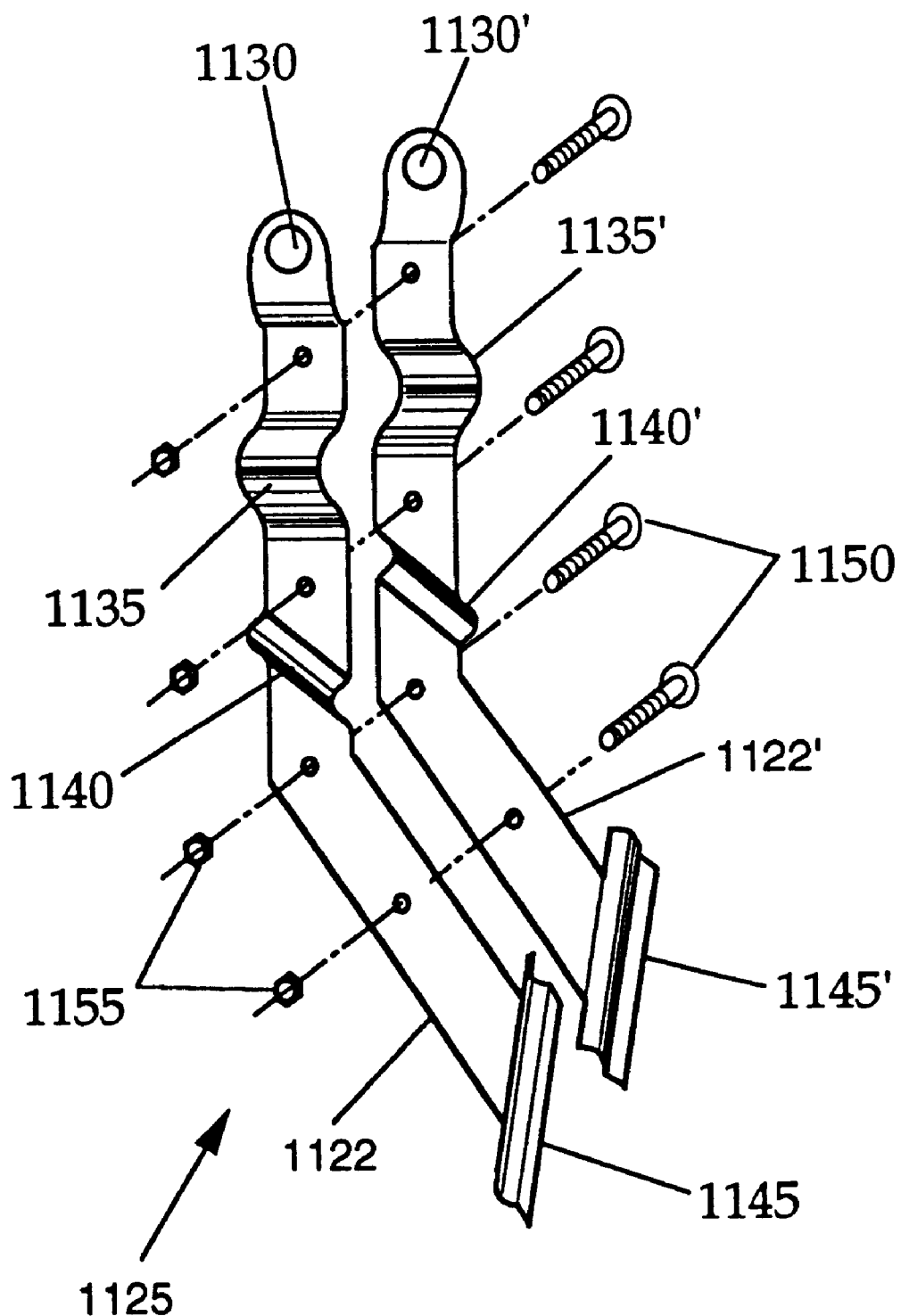

Securing device 1125 is depicted in more detail in FIG. 37. The opposed securing elements 1122, 1122' are preferably comprised of two substantially rigid bands, which may be composed of metal, polymer, or other materials. Fasteners, such as bolts and nuts, are then employed to hold the bands securely together. Each band 1122, 1122' includes a mounting hole 1130, 1130' proximate to its respective upper distal portion thereof. Preferably, each mounting hole has a diameter about one third of the diameter of spherical joint 1115 of FIG. 36a. Each band further includes a half-clasp 1145, 1145' of opposed curvature which is arranged to cooperate to releasably secure the stem 1128 of the distal finger-loop 1132 of the instrument handle 1068. Also provided are oppositely curved sections 1135, 1135' and 1140, 1140' positioned and oriented on the bands 1122, 1122' so as to secure respectively the sheath 1030 and guide tube 1050. Bolts 1150 and nuts 1155 fasten the bands together. The spring constant of the band material, the band curvature, and the bolt-hole positions are selected so as to provide sufficient force on spherical joint 1115 to prevent its unintended rotation and on the instrument handle 1068 to prevent unintended release.

Many other securing devices may be envisioned, it will be appreciated, to couple the endoscope, display, and instrument according to the present invention. It is intended that the use of alternative connecting devices would fall within the scope of this invention.

The embodiment described with reference to FIGS. 36 and 37 demonstrates the adaptation of one type of operating endoscope to function according to the present invention. Similarly, operating endoscopes of differing designs can be so adapted by the inclusion of means for enabling the handle of the endosurgical instrument to control the position and orientation of the endoscope, and by the attachment of a suitably positioned video display to the endoscope.

As demonstrated above with reference to FIGS. 8 through 13, in other embodiments of this invention, a rotational constraint is utilized to prevent the endoscope and display from rotating about the endoscope's longitudinal axis. In this arrangement, the surgeon may employ the instrument handle to freely rotate the instrument about its axis while using the handle to control and manipulate the position and orientation of the integrated surgical system. In accordance with this embodiment of the present invention, such a rotational constraint on the endoscope and display may be applied as well. For example, an instrument latching mechanism 395, such as that illustrated in FIGS. 8, 15, and 16, might be used to retain the instrument, rather than the clasp illustrated FIG. 36a and 37. As previously indicated, this latching arrangement also prevents independent instrument rotation. The endoscope and display may, for instance, be mounted on an articulated arm configured so as to allow the position and orientation of the endoscope and display to be varied while preventing their rotation about the instrument's longitudinal axis.

Figure 38:
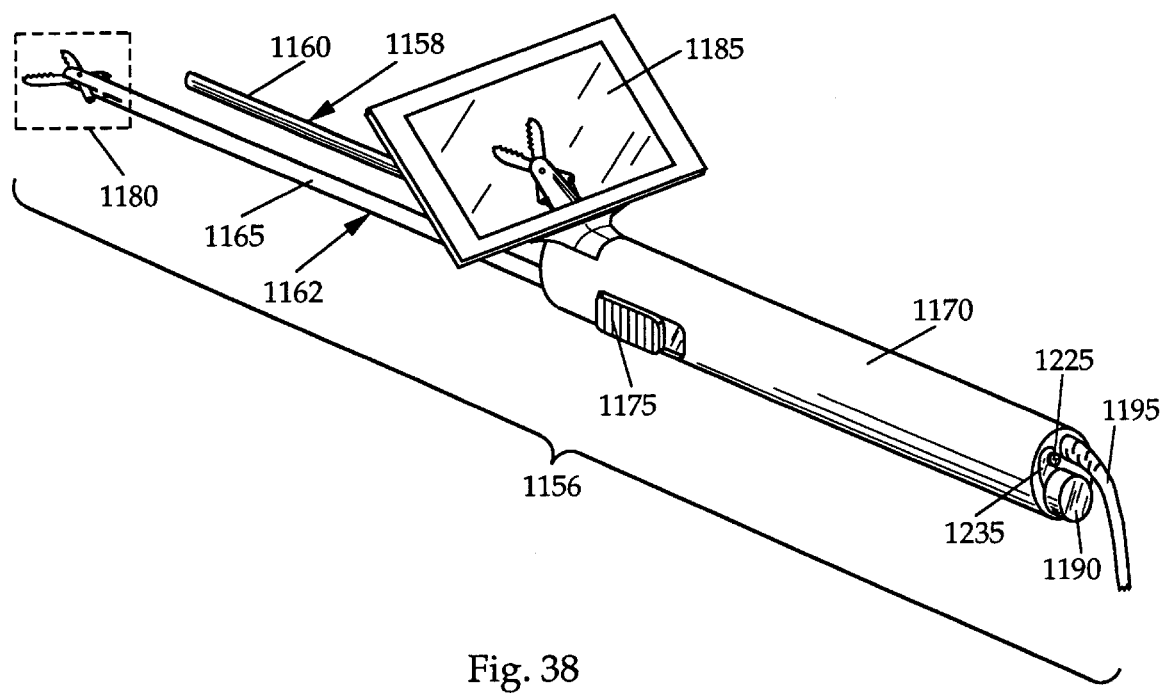
FIG. 38 is a top perspective view of an alternative embodiment endoscopic surgery system of the present invention comprising a handle portion, an endoscopic telescope projecting from the handle portion, an endosurgical instrument received within the handle portion and securable thereto, a finger-operated control for actuating the instrument, and a video display attached to the handle.

FIG. 38 illustrates yet another embodiment of the endosurgical system 1156 of the present invention, utilizing an endoscope 1158, having a telescope portion 1160, and an endosurgical instrument 1162 coupled to a common handle 1170. In this configuration, the endoscopic telescope 1160 and the endosurgical instrument 1162 are adapted to independently extend into the body part rather than within a common insertion tube or sheath, while being manipulated as a single unit. A flat-panel video display 1185 is included which is preferably mounted at a distal end of the handle 1170.

Figure 39A:
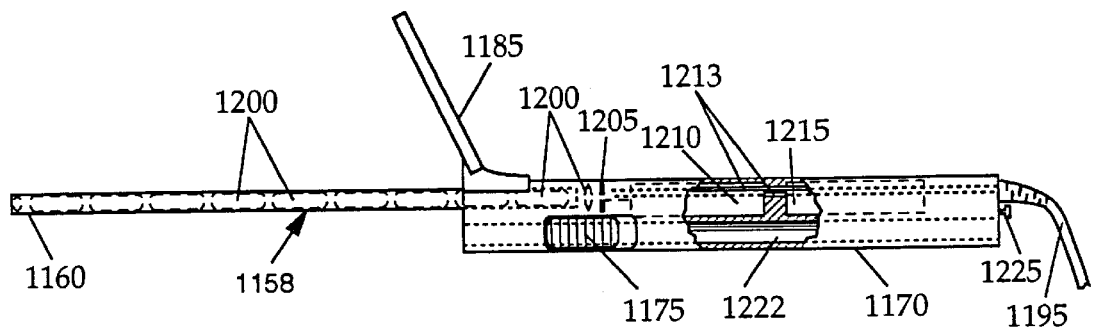
FIG. 39a is a side elevation view, partially broken away, of the handle portion, the endoscopic telescope, the video display, and the instrument actuator of the endoscopic surgery system of FIG. 38.

This video display 1170 is positioned relative the handle so that the image of the endeffector 1180 on the display, as viewed from the telescope portion 1160, emerges from the bottom of the display and is in proximity to and preferably substantially aligned with the actual end-effector. Accordingly, during operation and manipulation of the endosurgical system 1156, it will appear to the surgeon that he is directly viewing the actual end-effector 1180 unobscured by the body part. Consequently, the surgeon may have the impression of an open surgery. handle 1170 is preferably in the form of an elongated cylinder; however, other handle shapes may be substituted within the scope of this invention. As described below with reference to FIGS. 39a, 39b and 41, the handle 1170 contains endoscopic components of the endoscope 1158, such as optical elements 1260 and a video-image-detector 1205. These components operate in conjunction with the telescope 1160, extending distally from the distal face of the handle, to provide video image signals corresponding to the endoscopic field of view. Moreover, at least part of the electronic circuits associated with the video detector 1205 and display 1185 are located within handle 1170. FIG. 39*a* illustrates a side view of such an endosurgical system 1156, depicting internal as well as external features. Briefly, the handle 1170 further includes a finger-operated sliding control button 1175 which operably communicates with an internal actuation rod 1220 of the instrument 1162 to operate its end-effector 1180.

Endoscopic telescope 1160 of the endoscope 1158 contains optical elements 1200, which relay the image back to video image detector 1205. The video signals from the image detector are preamplified in signal processing module 1210 located in the handle. This module communicates through cable 1195 with external processing circuits, which communicate via cable 1195 with display-electronics module 1215, located in the handle. Cable 1195 preferably contains optical fibers 1213 (FIG. 39*a*) and electrical wires conduct light, video signals, and other electrical energy between the endoscopic surgical system 1156 of FIG. 38 and external units, such as those described with reference to FIGS. 1 and 17. An external light source (not shown) is connected to one or more optical fibers 1213 in the cable. These fibers terminate at the distal face of the telescope, from which location they illuminate the surgical site.

Figure 39B:
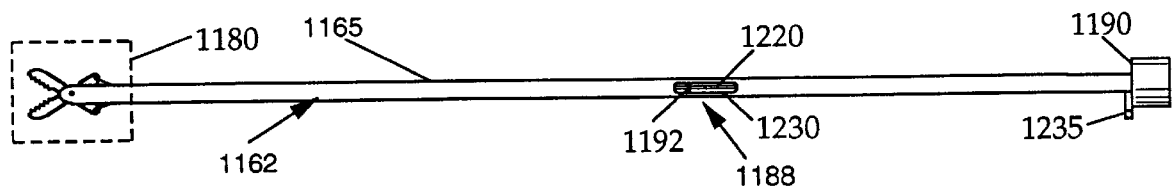
FIG. 39b is a side view of the endosurgical instrument of the endoscopic surgery system of FIG. 38, illustrating a window through which actuation of the end-effector is effected.
Figure 40:
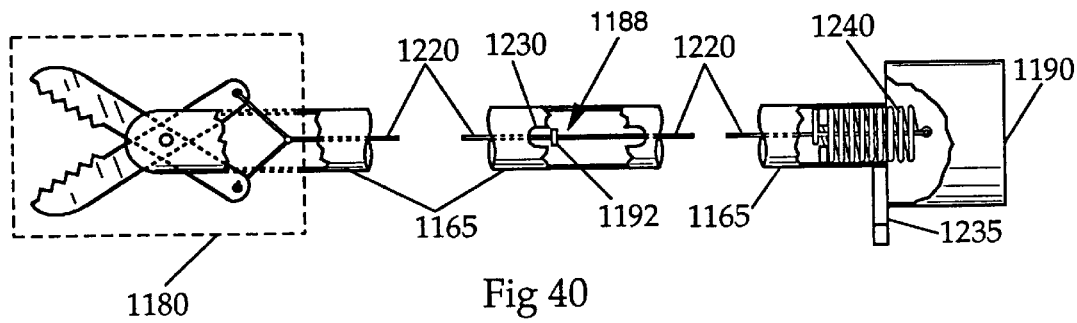
FIG. 40 is an enlarged, fragmentary, side elevation view, partially broken away, of the endosurgical instrument of FIG. 39b.
Figure 41:
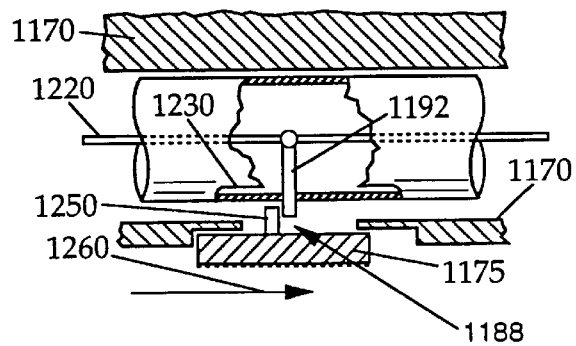
FIG. 41 is an enlarged, fragmentary, top plan view, partially broken away, of the coupling mechanism within the handle portion of the endoscopic surgery system.

As best illustrated in FIGS. 39*b*, 40, and 41, the endosurgical instrument 1162 of system 1156 preferably includes an elongated hollow cylindrical shaft 1165, an end-effector 1180, knob 1190 with engagement latch 1235, and an internal actuation rod 1220 operably coupled to the end-effector 1180. The endosurgical instrument of this system 1156 is removable coupled to the handle 1170 so that the instruments may be changed depending upon the desired end-effector required. Thus, while the end-effector 1180 is illustrated as a pair of graspers movable from a normally opened condition FIGS. 39*b* and 40) to a closed condition (not shown), it will be appreciated that the end-effector may be provided by scissors, needle drivers, or other device requiring mechanical actuation, and may be straight-ahead or angled.

The shaft 1165 and the end-effector 1180 are adapted to be slideably received in a bore 1222 extending longitudinally through handle 1170. When the instrument 1162 is fully inserted into bore 1222 of the handle 1170, an engagement latch 1235, extending radially outward from the shaft 1165 proximate to the knob 1190, will be positioned in alignment with a securing pin disposed on the proximal end of the handle. Upon clockwise rotation of the instrument about its longitudinal axis via knob 1190, a hooked portion of the engagement latch 1235 releasably engages securing pin 1225 to prevent the instrument from longitudinal withdrawal and rotation with respect to the handle during use.

To operate the end-effector 1180, a linkage mechanism 1188 is provided which operably couples the end-effector to the control button 1175 positioned on the handle 1170 during mounting of the instrument where the engagement latch 1235 rotational engages the securing pin 1225. FIGS. 39*b*, 40 and 41 best illustrate that the linkage mechanism 1188 includes an upstanding pin 1192 which is attached to internal actuation rod 1220 within instrument shaft 1165 and is rotated into alignment with a boss 1250 of the control button 1175 during mounting of the instrument 1162 to the handle 1170. The upstanding pin 1192 projects through an elongated opening 1230 in the hollow shaft 1165 by an amount sufficient to enable engagement with the control button boss 1250. This engagement enables the user to control the end-effector by finger motion, via button 1175, as is further described below with reference to FIGS. 40 and 41.

Once the linkage mechanism 1188 is engaged, the end-effector 1180 may be selectively manipulated through the sliding operation of button 1175. Upon sliding of the control button 1175 in the direction of arrow 1260 (FIG. 41), the boss 1250 contacts the pin 1192 which also urges the actuation rod 1220 in the direction of arrow 1260 as well. Consequently, the axial movement of rod 1220 through shaft 1165 urges the pivotally connected jaws the grasper end-effector 1180 to move from the opened condition to the closed condition. A compression spring 1240 or the like is coupled to the proximal end of the actuation rod 1220 which biases the jaws of the grasper toward the opened condition. Thus, closure of the end-effector results when a lateral force acting upon button 1175 and in the direction of arrow 1260 overcomes the spring force. Upon removal of the sufficient lateral force, the spring 1240 will urge the end-effector 1180 back toward the opened condition.

It is recognized that it may be advantageous to reposition the rotational orientation of the end-effector 1180 to perform a desired surgical maneuver. Ferrule-operated mechanisms, for example, may be employed to rotationally reposition the endosurgical end-effector. The inclusion of these type mechanisms to such rotational adjustment in embodiments of the present invention is within the scope of this invention.

Figure 42:
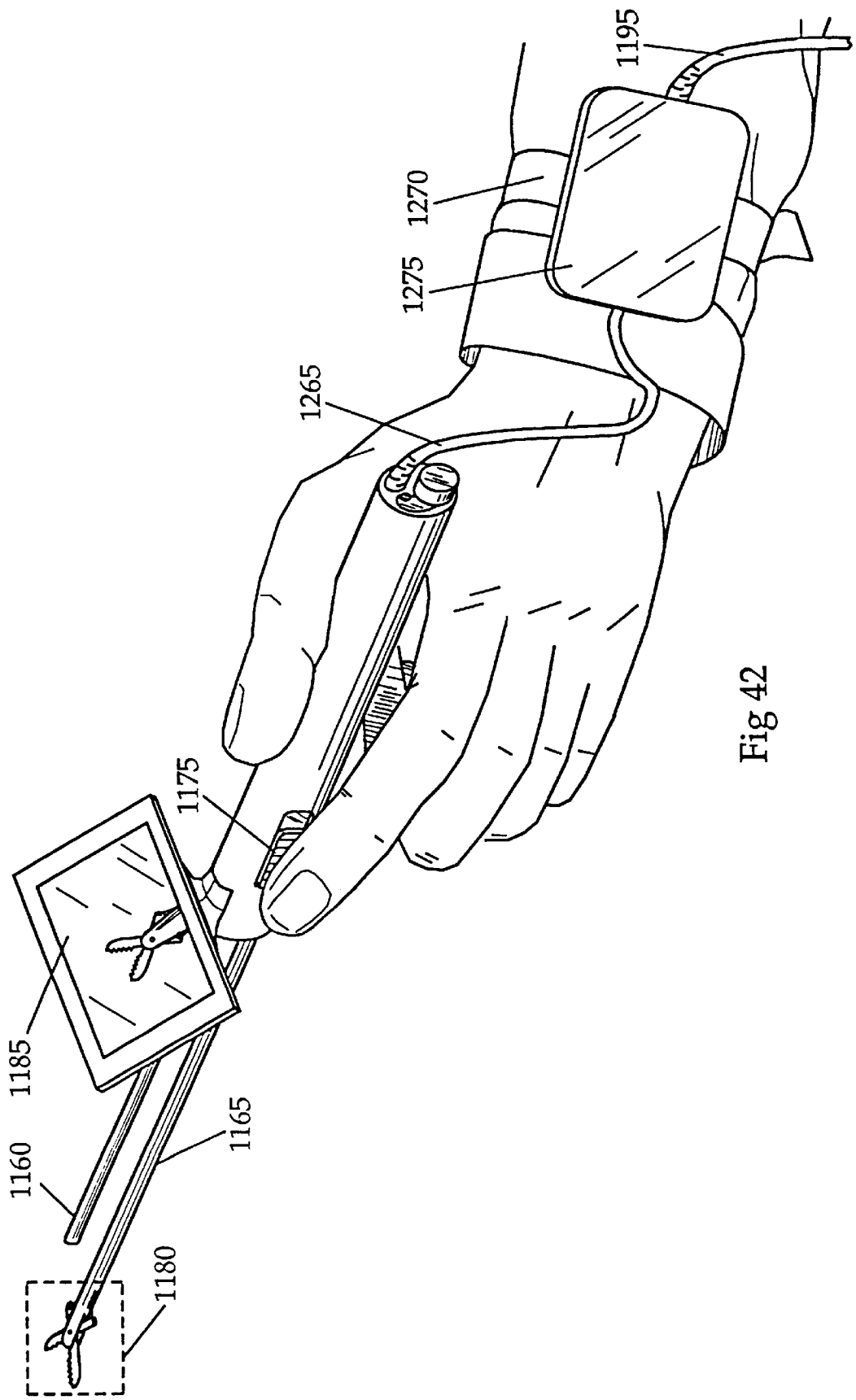
FIG. 42 is a top perspective view of the endosurgical system of FIG. 38, and having a lightweight video electronics module coupled to a wrist strap which in turn is secured to a surgeon's wrist.

FIG. 42 illustrates another embodiment of the endosurgical system of FIG. 38.

Because endosurgical manipulation of tissues often requires the surgeon to have a high degree of touch sensitivity, it is advantageous to minimize the weight of the hand-supported portion of the endoscopic surgery system and to minimize any extraneous forces that might be exerted upon it. The embodiment of FIG. 42 incorporates unique features directed to these ends. A wrist strap 1270 is secured to cable 1265 emanating from the proximal end of the instrument. The strap is releasably secured to the surgeon's wrist during use through a fastener (e.g., VELCRO). Thereby, the weight of the cable and any forces exerted upon the cable are supported by the wrist and are not transferred to the instrument or the surgeon's fingers.

A further reduction of the weight of the hand-supported portion of the system is achieved by moving the electronics, housed within the handle according to FIG. 39, to 30 an electronics module 1275 affixed to the wrist strap. Electrical connections between the module and the internal video image detector and the display are carried within cable 1265. Electrical connections from module 1275 and an external signal processing and control unit are carried within cable 1195, which also is secured to the wrist strap, either directly or through attachment to module 1275. Optical fibers conducting light from an external source to telescope 1160 are carried within cable 1195, through or around the electronics module, and through cable 1265 to the telescope.

It is noted that, in general, certain portions of the electronics circuits that operate in conjunction with video image detectors and flat-panel displays must be in close proximity to these devices, and thus cannot be located in an external electronics unit, which might typically be at the end of a cable one to two meters in length. The wrist-mounted module is close enough to the video detector and display to avoid the difficulties associated with long cables. Moreover, removing the electronics from the handle reduces constraints on sterilization and reduces the cost of the hand-held portion, which may then be inexpensive enough to be disposable, thereby eliminating the requirement for sterilization prior to reuse. Additionally, a video display may be attached to the wrist strap, on which endoscopic images or other data may be displayed for the surgeon's benefit. In all of the foregoing embodiments, the size of the image as compared with the dimensions of the actual object field may be readily modified to accommodate the operator's preference, either by altering the endoscope optics or by electronically scaling the video image; both are within the scope of the present invention.

In all of the foregoing embodiments, the use of monoscopic video has been indicated, wherein monoscopic means that a single two-dimensional image is formed and presented to both eyes. Stereoscopic video endoscopy is well known in the art and the substitution of stereoscopic for monoscopic video is within the scope of all of the embodiments of this invention. Stereoscopic video endoscopes made by Richard Wolf Medical Instruments, in Rosemont, utilizes time-sequential presentation of left- and right-eye images derived from special endoscopes with side-by-side optical channels. The operator wears special glasses with electrically switchable transmissivity. The left and right windows are made alternately transparent and opaque in synchrony with the images from each side of the laparoscope. Stereoscopic imaging with a monoscopic endoscope and special signal processing is sold by Automated Medical Products Corp. New York, N.Y. Stereoscopic video projection of the virtual image to an arbitrary region behind the display is well known and readily achieved by adjusting the relative left/right positions of the left-eye and right-eye images as they appear in the display, using known video signal processing methods. In this manner, substitution of stereoscopic video in the present invention enables the operator to perceive the image of the instrument tip and the tissues to lie behind the display, for example, in substantially the same spatial position in which they would be observed were they directly visible.

This enhances the illusion of reaching into an operative site under direct visualization, which further facilitates dexterous manipulation. If stereoscopic imaging is used, the display may be set perpendicular to the instrument axis, and ambiguity as to direction and motion will be reduced as compared to a monoscopic display.

Endoscopes are made that have fields of view that are symmetric about the endoscope axis ("straight ahead" or "0°" endoscopes) and that have angularly offset fields of view (e.g., "30°" and "70°" endoscopes). The use of straight-ahead and angled endoscopes are both within the scope of the present invention.

Whereas in the illustrated embodiments only rigid endoscopes are shown, it is understood that embodiments incorporating flexible endoscopes and flexible endoscopic instruments which pass therethrough are within the scope of this invention.

Whereas endoscopes and instruments of specific dimensions have been selected so as to illustrate preferred embodiments for certain medical applications, the invention is not limited as to endoscopes and instruments of these sizes. In particular, smaller endoscopes and instruments will be found to be preferable for other medical applications.

Whereas, in the foregoing, hand-powered grasping and cutting instruments have been shown, this invention is not limited with regard to the types of instruments that may be utilized, which also include but are not limited to articulated or flexible hand-powered instruments, electrocautery and laser photocoagulation devices, suctioning devices for the evacuation of fluids and soft tissues, and mechanically powered devices for removal of soft and hard tissues, which may, for example, be rotary or oscillatory in motion and driven by pneumatic or hydraulic means or by electrical or ultrasonic motors. The hand operated control means may be, for example, in the form of a pistol grip with a trigger that actuates electrically or mechanically controlled instruments.

Whereas, it is desirable to make the weight and inertia of the hand-held instrument portion of this invention as low as possible, all measures to reduce its size and mass, such as the use of special light-weight materials, the removal of electronic modules from the hand-held instrument to the electronics units, and the reduction in size of any or all of its components is within the scope of this invention.

Although the present invention has been shown and described with respect to preferred embodiments, the foregoing and other changes and modifications which are obvious to a person skilled in the art to which the invention pertains are deemed to be within the spirit and scope of the invention.

I claim:

1. An endoscopic surgical system for use in endoscopic surgery comprising:

an endosurgical instrument having an elongated shaft and an end-effector operably mounted to a distal end of said shaft;

a video endoscope device having an elongated telescope portion containing a distal viewing face;

a coupling device coupling the instrument to the endoscope device in a manner substantially maintaining the relative position of the elongated shaft adjacent the telescope portion such that the endoscope viewing face is rearward of the distal end effector to view the distal end-effector from a position along said shaft;

a handle portion operably coupled to the coupling device in a manner enabling said distal end-effector and said viewing face to be manually positioned as a single unit during endoscopic surgery, and said handle portion being further configured to manually operate the end-effector, and a video display device operably coupled to and fixed relative to the endoscope device at a viewing angle and location therealong wherein an image of the end-effector displayed on said display device appears to be a substantially direct view of said end-effector that is positioned in-line with the insertion shaft.

2. The endoscopic surgical system according to claim 1 further including:

a rotation preventing mechanism coupled between the end-effector and the coupling device to substantially prevent axial rotation thereof relative to the distal viewing face.

3. The endoscopic surgical system according to claim 1 wherein, the video display device is a flat panel display.

4. The endoscopic surgical system according to claim 1 wherein, said coupling device includes a securing device mounting the instrument shaft, the handle portion and the telescope portion together for manipulation as a single unit.

5. The endoscopic surgical system according to claim 4 wherein, said handle portion is integrally formed with said endosurgical instrument, and said securing device is adapted to rigidly mount the handle portion to the instrument shaft.

6. The endoscopic surgical system according to claim 5 wherein, said securing device includes a pair of opposed securing elements formed to releasably engage the handle portion and the telescope portion therebetween.

7. The endoscopic surgical system according to claim 5 further including:

an adapter device coupled to the telescope portion of the endoscope and providing a bore portion formed and dimensioned for receipt of the instrument elongated shaft therethrough for alignment of the end-effector in the field of view of the distal viewing end.

8. The endoscopic surgical system according to claim 7 further including:
a guide tube in axial communication with said bore portion for guided insertion of said elongated shaft through said guide tube and into said bore portion.

9. The endoscopic surgical system according to claim 8 further including:
said guide tube is supportively coupled to the securing device.

10. The endoscopic surgical system according to claim 9 further including:
a joint device releasably mounting the display device to the securing device.

11. The endoscopic surgical system according to claim 9 wherein,
said securing device includes a pair of opposed securing elements formed to releasably engage the handle portion and the telescope portion therebetween.

12. The endoscopic surgical system according to claim 11 further including:
a spherical joint member positioned between the opposed securing elements for movably mounting the display device to the securing device at one of a plurality of positions.

13. The endoscopic surgical system according to claim 12 wherein,
the video display device is a flat panel display.

14. The endoscopic surgical system according to claim 8 further including:
a latching arrangement for releasably latching the received elongated shaft to one of the endoscope and the guide tube such that the received elongated shaft rotates freely about its axis within the guide tube and bore portion, but cannot be advanced or withdrawn therefrom.

15. The endoscopic surgical system according to claim 1 wherein,
said coupling device is configured to position the elongated shaft of the instrument substantially parallel to and adjacent to the telescope portion.

16. The endoscopic surgical system according to claim 1 wherein,
said coupling device is integrally formed with said handle portion.

17. The endoscopic surgical system according to claim 16 wherein,
said handle portion defines a bore formed and dimensioned for receipt of the instrument elongated shaft therein.

18. The endoscopic surgical system according to claim 17 wherein,
said bore extends longitudinally through said handle portion from a proximal end to a distal end thereof.

19. The endoscopic surgical system according to claim 17 further including:
a latch assembly releasably mounting the instrument to the handle portion.

20. The endoscopic surgical system according to claim 19 wherein,
said latch assembly is adapted for movement between an unlatched condition, enabling removal of said elongated shaft from said bore, and a latched condition, releasably latching the instrument to the handle portion.

21. The endoscopic surgical system according to claim 20 wherein,
said latch assembly is adapted to rotate between the unlatched condition and the latched condition.

22. The endoscopic surgical system according to claim 21 wherein,
said latch assembly includes a n engagement latch mounted to one of the elongated instrument and the handle portion, and a pin member mounted to the other of the handle portion and the elongated instrument for latched coupling between the latched and unlatched conditions.

23. The endoscopic surgical system according to claim 20 further including: a linkage assembly operably coupling the end-effector of the instrument to an actuation device of the handle portion for actuation of the end-effector when said latch assembly is moved to said latched condition.

24. The endoscopic surgical system according to claim 23 wherein,
said linkage assembly includes an actuation rod disposed longitudinally along said elongated shaft, and coupled to said end-effector for movement between a first position and a second position.

25. The endoscopic surgical system according to claim 24 wherein,
said linkage assembly further includes a boss member coupled to said actuation rod which operably engages said actuation device when said instrument is moved from the unlatched condition to the latched condition.

26. The endoscopic surgical system according to claim 24 wherein, latch assembly is adapted to rotate between the unlatched condition and the latched ondition.

27. The endoscopic surgical system according to claim 26 wherein,
said linkage assembly further includes a boss member coupled to said actuation rod which operably engages said actuation device upon rotation of said instrument from the unlatched condition to the latched condition, said latch assembly includes an engagement latch mounted to one of the elongated instrument and the handle portion, and a pin member mounted to the other of the handle portion and the elongated instrument for latched coupling upon rotation of said instrument from the unlatched condition to the latched condition.

28. The endoscopic surgical system according to claim 24 further including: a biasing device operably coupled to said actuation rod to bias said end-effector toward one of the first position and the second position.

29. The endoscopic surgical system according to claim 28 wherein, said biasing device is provided by a compression spring.

30. The endoscopic surgical system according to claim 1 further including: a wrist mounted electronic module operably coupled, to said endoscope device and containing at least a portion of the optical electronics thereof.

31. The endoscopic surgical system according to claim 16 wherein,
the video display device is a flat panel display mounted to a distal portion of the integral handle portion and coupling device.

32. The endoscopic surgical system according to claim 1 further including:
a latching arrangement for releasably latching the elongated shaft of the instrument to one of the endoscope device and the coupling device such that the elongated shaft rotates freely about its axis, but cannot be advanced or withdrawn therefrom.

33. A video endoscope system for use by a surgeon in endoscopic surgery:
a surgical instrument having an elongated shaft and an end-effector;
an elongated endoscope device including a telescope portion having a distal viewing face;

a coupling device securably coupling the instrument to the endoscope device in a manner substantially maintaining the relative position of the elongated shaft adjacent the telescope portion to facilitate viewing of the end-effector of the surgical instrument by said viewing face;

a video display mounted to the coupling device and adapted to display an image of the end-effector viewed by the distal viewing face; and a handle portion operably coupled to the surgical instrument for actuation of the end effector, and rigidly coupled to the coupling device for simultaneous positioning of end-effector and said endoscope viewing face as a unit, independent of the operation of the end-effector and in a manner substantially maintaining said end-effector in the field of view of said viewing face during operation and manipulation of the handle such that a surgeon operating the endoscope system by the handle will view and perceive the image of the end-effector on the video display as being directly viewed at a true position of the end-effector from the perspective of the surgeon, enabling the surgeon to effectively perform remote surgery with the hand-eye coordination approximating that of open surgery.

34. The video endoscope system according to claim 33 wherein, said coupling device includes a pair of opposed securing elements formed to releasably engage the handle portion and the telescope portion therebetween.

35. The video endoscope system according to claim 34 further including:

an adapter device coupled to the telescope portion of the endoscope and providing a bore portion formed and dimensioned for receipt of the instrument elongated shaft therethrough for alignment of the end-effector in the field of view of the distal viewing end.

36. The video endoscope system according to claim 35 wherein, a guide tube in axial communication with said bore portion for guided insertion of said elongated shaft through said guide tube and into said bore portion.

37. The video endoscope system according to claim 36 further including:

said guide tube is supportively coupled between the securing elements.

38. The video endoscope system according to claim 37 further including:

a joint device releasably mounting the display device between the securing elements.

39. The video endoscope system according to claim 38 wherein, the video display device is a flat panel display.

40. The video endoscope system according to claim 33 wherein, said coupling device is integrally formed with said handle portion.

41. The video endoscope system according to claim 40 wherein, said handle portion defines a bore formed and dimensioned for receipt of the instrument elongated shaft therein.

42. The video endoscope system according to claim 41 further including:

a latch assembly releasably mounting the instrument to the handle portion.

43. The video endoscope system according to claim 42 wherein, said latch assembly is adapted for movement between an unlatched condition, enabling removal of said elongated shaft from said bore, and a latched condition, releasably latching the instrument to the handle portion.

44. The video endoscope system according to claim 43 wherein, said latch assembly includes an engagement latch mounted to one of the elongated instrument and the handle portion, and a pin member mounted to the other of the handle portion and the elongated instrument for latched coupling between the latched and unlatched conditions.

45. The video endoscope system according to claim 44 further including:

a linkage assembly operably coupling the end-effector of the instrument to an actuation device of the handle portion for actuation of the end-effector when said latch assembly is moved to said latched condition.

46. A method of performing endoscopic surgery comprising the steps of:

providing an endosurgical instrument having an elongated shaft and an end-effector operably mounted to a distal end of said shaft;

providing a video endoscope device having an elongated telescope portion containing a distal viewing face;

coupling the endosurgical instrument to the endoscope device through a coupling device in a manner substantially maintaining the relative position of the elongated shaft adjacent the telescope portion such that the endoscope viewing face is rearward of the distal end effector to view the distal end-effector from a position along said shaft;

inserting the end-effector and the distal viewing face simultaneously into a body part through a natural orifice or incision;

displaying an image of the end effector from the endoscope distal viewing face on a video display operably coupled to and fixed relative to the endoscope device; and operating a handle portion operably coupled to the surgical instrument for actuation of the end effector, and rigidly coupled to the coupling device for simultaneous positioning of end-effector and said endoscope viewing face as a unit, independent of the operation of the end-effector and in a manner substantially maintaining said end-effector in the field of view of said viewing face during operation and manipulation of the handle such that a surgeon operating the instrument by the handle will view and perceive the image of the end-effector on the video display as being directly viewed at a true position of the end-effector from the perspective of the surgeon, enabling the surgeon to effectively perform remote surgery with the hand-eye coordination approximating that of open surgery.

* * * * *